United States Patent
Janna et al.

(10) Patent No.: US 12,396,767 B2
(45) Date of Patent: Aug. 26, 2025

(54) IMPLANTABLE MOTORIZED BONE ADJUSTMENT DEVICES

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Sied W. Janna, Memphis, TN (US); Darren J. Wilson, Hull (GB)

(73) Assignees: SMITH & NEPHEW, INC, Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 191 days.

(21) Appl. No.: 18/283,765

(22) PCT Filed: Mar. 22, 2022

(86) PCT No.: PCT/US2022/021277
§ 371 (c)(1),
(2) Date: Sep. 22, 2023

(87) PCT Pub. No.: WO2022/204096
PCT Pub. Date: Sep. 29, 2022

(65) Prior Publication Data
US 2024/0164816 A1      May 23, 2024

Related U.S. Application Data

(60) Provisional application No. 63/165,308, filed on Mar. 24, 2021.

(51) Int. Cl.
*A61B 17/72* (2006.01)
*A61B 17/00* (2006.01)

(52) U.S. Cl.
CPC ............ *A61B 17/7216* (2013.01); *A61B 2017/00022* (2013.01); *A61B 2017/00398* (2013.01); *A61B 2017/00734* (2013.01)

(58) Field of Classification Search
CPC . A61B 17/72; A61B 17/7216; A61B 17/7258; A61B 2017/00022; A61B 2017/00398
(Continued)

(56) References Cited

U.S. PATENT DOCUMENTS

| 6,245,075 B1 | 6/2001 | Betz |
| 9,138,266 B2* | 9/2015 | Stauch ............... A61B 17/7216 |
| 9,943,345 B2* | 4/2018 | Nill ..................... A61B 17/7016 |

FOREIGN PATENT DOCUMENTS

| EP | 2570092 A2 | 3/2013 |
| EP | 2915496 A1 | 9/2015 |

(Continued)

OTHER PUBLICATIONS

International Search Report and Written Opinion for the International Application No. PCT/US2022/021277, mailed Jun. 9, 2022, 9 pages.

*Primary Examiner* — Eduardo C Robert
*Assistant Examiner* — Christina Negrellirodriguez
(74) *Attorney, Agent, or Firm* — KDW Firm PLLC

(57) ABSTRACT

Methods and devices for bone adjustment, such as limb lengthening, are disclosed. For example, in one embodiment, a bone adjustment device may include a proximal portion configured to attach to a first bone portion, a distal portion configured to attach to a second bone portion, a motorized drive assembly, a control circuitry operably coupled to the motorized drive assembly, the motorized drive assembly and the control circuitry being hermetically sealed within a motor compartment, a driving element having a first end operatively coupled to the motorized drive assembly and a second end operatively coupled to the distal (Continued)

portion, the control circuitry is operative to receive wireless control signals from an external computing device, the motorized drive assembly is configured to be actuated based on the control signals to force rotation of the driving element to cause movement of the distal portion away from the proximal portion. Other embodiments are described.

15 Claims, 24 Drawing Sheets

(58) Field of Classification Search
USPC .............................................. 606/62, 63, 68
See application file for complete search history.

(56) References Cited

FOREIGN PATENT DOCUMENTS

| | | | |
|---|---|---|---|
| EP | 3581130 | A1 | 12/2019 |
| WO | 2016172806 | A1 | 11/2016 |
| WO | 2018017591 | A1 | 1/2018 |

\* cited by examiner

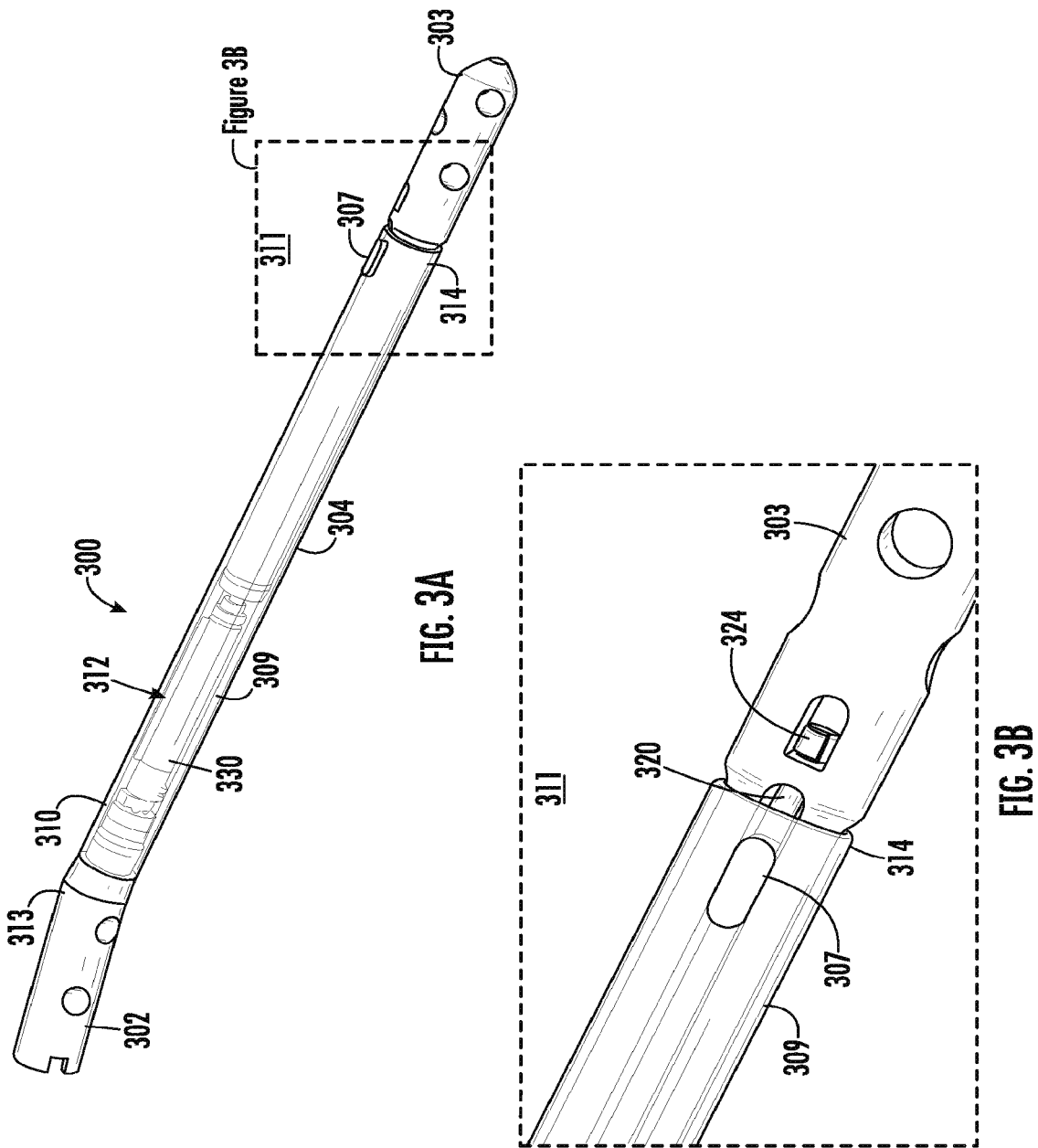

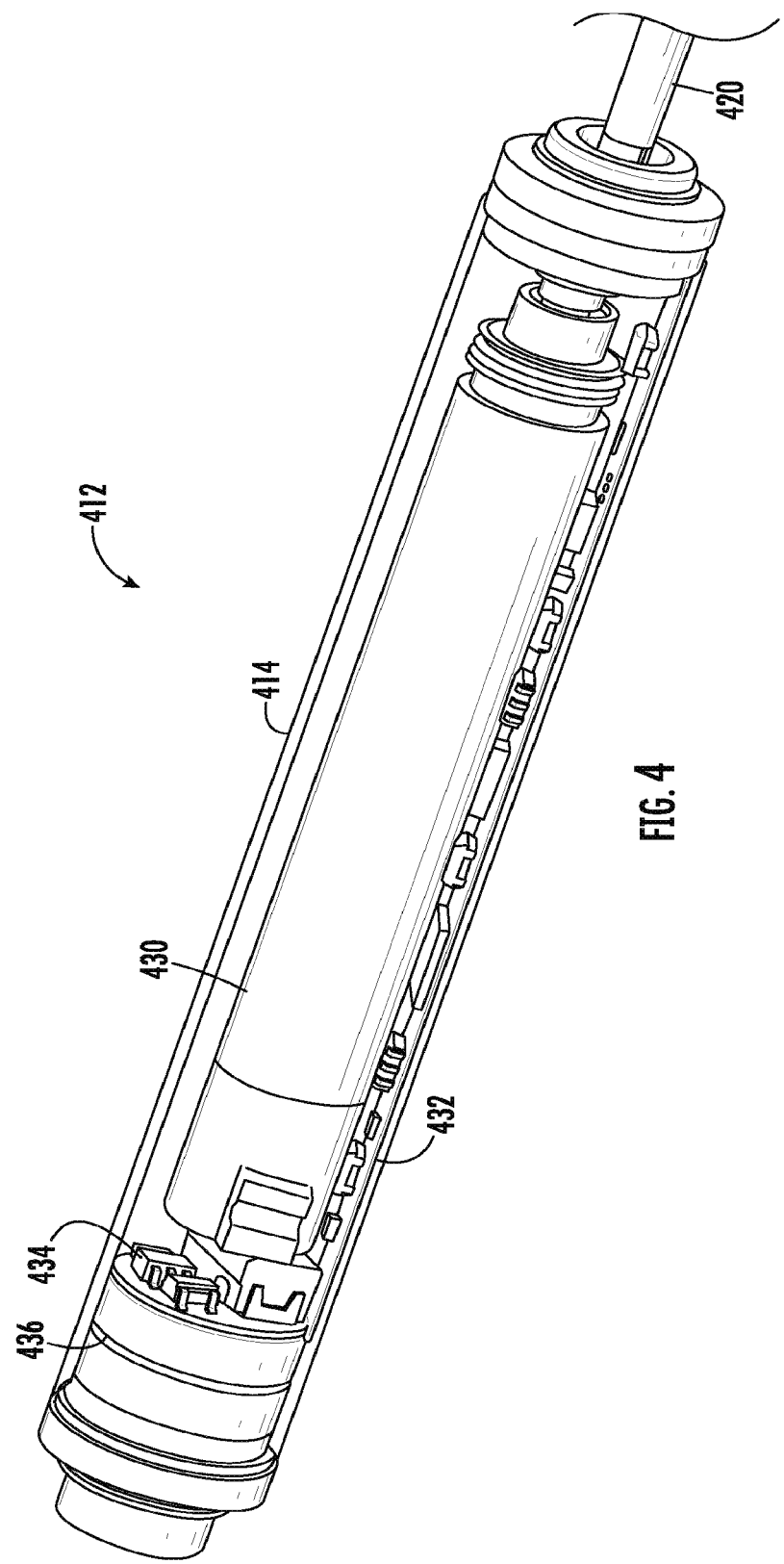

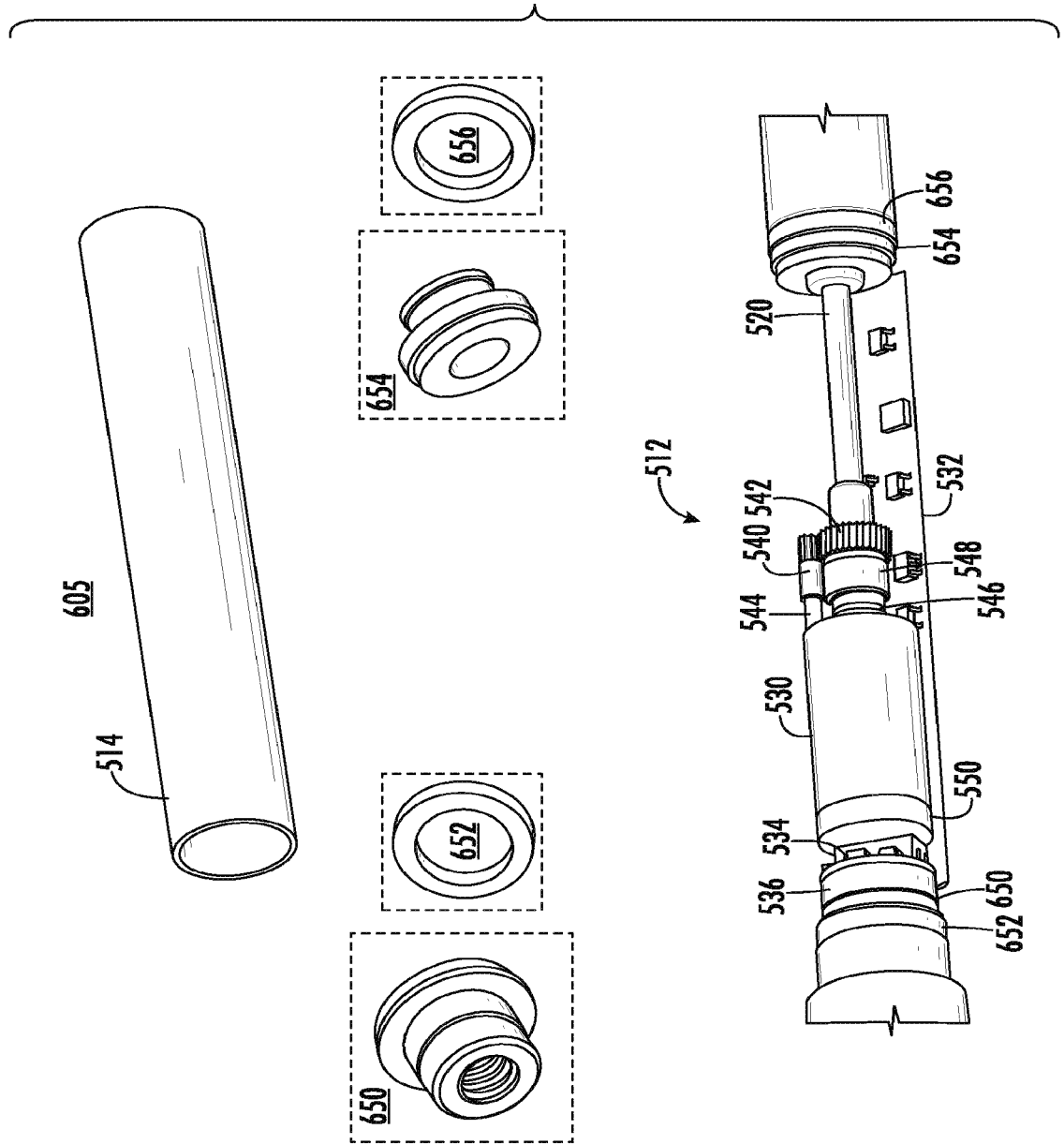

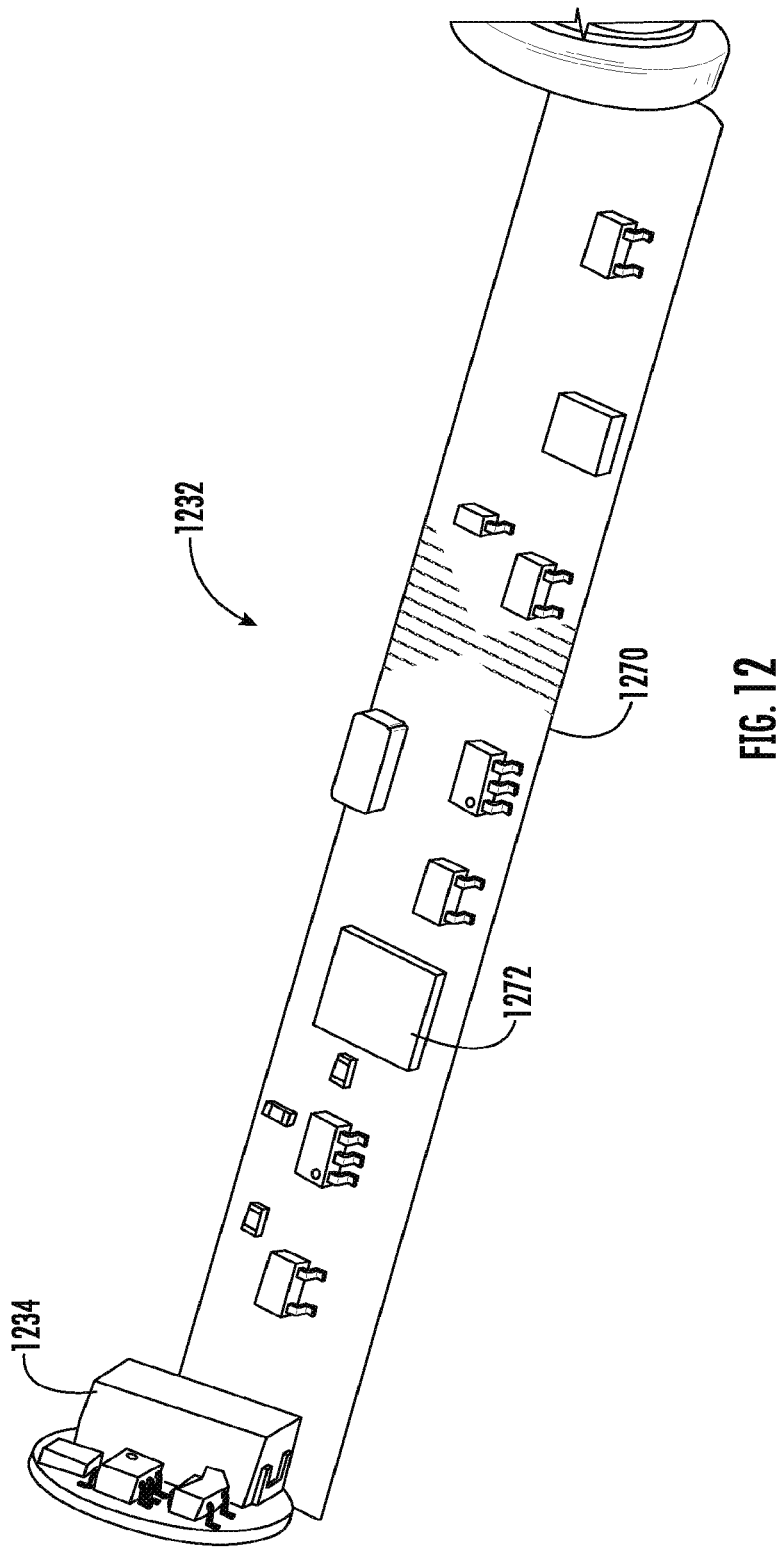

FIG. 15A

IMPLANTABLE MOTORIZED BONE ADJUSTMENT DEVICES

CROSS-REFERENCE TO RELATED APPLICATION

This application is a National Phase filing of International Application No. PCT/US2022/021277, filed Mar. 22, 2022, which application claims the benefit of U.S. Provisional Patent Application Ser. No. 63/165,308, filed Mar. 24, 2021, and titled "Implantable Motorized Bone Adjustment Devices," the entire contents of each application is hereby incorporated by reference in its entirety.

FIELD OF THE DISCLOSURE

The present disclosure is directed to bone adjustment methods, systems, and devices, including limb lengthening nails, and more particularly to hone adjustment devices with a motorized drive mechanism.

BACKGROUND

Bone adjustment or fixation devices may be used in orthopedic procedures to adjust the position, orientation, geometry, and/or length of a bone. Traditional external or percutaneous fixation devices may be cumbersome, painful, and produce large residual scars. In addition, percutaneous fixation may introduce additional complications, such as relatively high infection rates.

Internal or implantable fixation devices may be mounted on or within patient boney anatomy, such as a femur or tibia. One form of an implantable reconfigurable bone adjustment device is a limb lengthening nail (LLN) configured for implantation in the intramedullary (IM) canal of a long bone and subsequently manipulated to adjust the length of the bone. In general, conventional LLNs and other internal fixators may include two connected, but separate segments that are attached to opposing portions of bone divided by a cut (i.e., an osteotomy or corticotomy). One segment may be stationary and the other segment may be forced to move the divided portions of bone apart to cause bone growth and, therefore, lengthening. The effectiveness of conventional LLNs and other internal fixators has been limited due to the cumbersome and complicated parts required to move the segments. In addition, conventional LLNs and other internal fixators are typically not full weight hearing and have unacceptable failure rates, which causes them to be difficult for patients.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides implantable bone adjustment devices, including, without limitation, limb lengthening devices. A non-limiting example of a bone adjustment device may be or may include an orthopedic distraction device configured for extending bones or bridging a gap in a bone. In some embodiments, a bone adjustment device may be configured as a limb lengthening nail (LLN).

Internal bone adjustment devices according to some embodiments may include a telescopic nail having an internal motor operative to drive at least one portion of the nail to increase (or decrease) the length of the nail and, therefore, move a corresponding portion of patient bone. For instance, a bone adjustment device may be configured to fit into the medullary canal of a human femur or tibia. As described in more detail below, through telescopic motion between two mating parts, the bone adjustment device can extend axially inside a dissected bone, for example, to elongate it to a desired length. In various embodiments, the hone adjustment device may be actuated via an electrical gear motor drive system, which may be energized and controlled from an internal power source (for example, a coin cell battery) without any direct physical connection or cabling outside of the patient. The bone adjustment device may be configured to withstand relatively large axial forces (for example, forces with a magnitude of 2000 N caused be exertion of extending the muscles), especially during the late stages of the distraction process. In addition, since the bone adjustment device is intended to be used inside the human body, proper insulation from the surrounding body fluids must be provided. Accordingly, some embodiments provide hermetic sealing of the motor, power, and other elements that power and/or actuate the bone adjustment device.

For example, in some embodiments, the bone adjustment device may include a drive assembly or mechanism in the form of a hermetically encapsulated electric geared motor-drive system embedded in a telescopic nail that drives the telescope apart. In various embodiments, the motor-drive system may include a gear and drive shaft mechanism operative to convert the rotation of the motor into an axial movement with high force. In some embodiments, the geared motor may turn in both directions, allowing the bone adjustment device to perform lengthening and compression procedures. In some embodiments, position control may be achieved using an encoder and/or sensor to control movement of one or more portions of the bone adjustment device at any given time. Non-limiting examples of an encoder or sensor may include an optical encoder, an electrically adapted optical incremental encoder, an infrared (IR) sensor, an IR line tracking sensor, and/or the like.

In exemplary embodiments, the bone adjustment device may be configured to receive wireless signals, for instance, for direct control and/or to upload prescription plans. In some embodiments, the bone adjustment device may be configured to transmit wireless signals, for example, to provide status or operational information or report status to a companion or adjustment application. Other features are described. Embodiments are not limited in this context.

In one embodiment, a hone adjustment device may include a proximal portion configured to attach to a first bone portion, a distal portion configured to attach to a second bone portion, and a motorized drive assembly operative to move the distal portion responsive to at least one control signal.

In one embodiment, a bone adjustment device may include a proximal portion configured to attach to a first bone portion, a distal portion configured to attach to a second bone portion, a motorized drive assembly, a driving element having a first end operatively coupled to the motorized drive assembly and a second end operatively coupled to the distal portion, wherein actuation of the motorized drive assembly forces rotation of the driving element to cause movement of the distal portion away from the proximal portion.

In one embodiment, a bone adjustment device may include a proximal portion configured to attach to a first bone portion, a distal portion configured to attach to a second bone portion, a motorized drive assembly, a control circuitry operably coupled to the motorized drive assembly, the motorized drive assembly and the control circuitry being hermetically sealed within a motor compartment, a driving element having a first end operatively coupled to the motorized drive assembly and a second end operatively coupled to the distal portion, wherein the control circuitry is operative to receive wireless control signals from an external computing device, wherein the motorized drive assembly is configured to be actuated based on the control signals to force rotation of the driving element to cause movement of the distal portion away from the proximal portion.

In one embodiment, a method for adjusting a bone of a patient may include implanting a bone adjustment device in the bone of the patient, in which the bone adjustment device may include a proximal portion configured to attach to a first hone portion, a distal portion configured to attach to a second bone portion, a motorized drive assembly, a control circuitry operably coupled to the motorized drive assembly, the motorized drive assembly and the control circuitry being hermetically sealed within a motor compartment, a driving element having a first end operatively coupled to the motorized drive assembly and a second end operatively coupled to the distal portion, wherein the control circuitry is operative to receive wireless control signals from an external computing device, wherein the motorized drive assembly is configured to be actuated based on the control signals to force rotation of the driving element to cause movement of the distal portion away from the proximal portion, and providing control instructions to the bone adjustment device using the external computing device.

In one embodiment, an apparatus may include a storage device storing instructions and logic coupled to the storage device, the logic, in response to executing the instructions, may operate to provide control instructions to control circuitry of a bone adjustment device to cause the bone adjustment device to actuate a motorized drive assembly to perform an adjustment process.

In some embodiments, the distal portion may be configured to be slidably disposed within a hollow middle section of the proximal portion. In various embodiments, the proximal portion may include an outer housing arranged to enclose the motor compartment.

In various embodiments, the adjustment device may be configured as a limb lengthening nail. In exemplary embodiments, the adjustment device may be configured as an intramedullary (IM) nail.

In some embodiments, the adjustment device may include a power system having one or more of at least one battery or a charging circuit to provide sufficient power to the motorized drive assembly. In various embodiments, the power system may provide sufficient power to other components, such as an encoder, sensors, and/or the like. In exemplary embodiments, the power system may enable firmware updates without causing adjustment system resets, such as any micro-controller, MCU, control circuitry (e.g., motor control circuitry), or similar component resets. In some embodiments, the at least one battery may be a lithium ion coin cell battery. In various embodiments, the at least one battery may be a lithium ion battery (for example, as a primary power source). In various embodiments, an external computing device (for instance, a smartphone, personal computer (PC), and/or the like) may act as a power or charging source.

A typical implantable bone adjustment device may not require a large amount of power to function. The amount of power needed may depend on the device's functions and voltage specifications, which may be as little as 2-3 volts. Therefore, devices according to some embodiments may be configured to, among other things, minimize the power consumption within the device circuit components and, in some embodiments, to additionally increase device efficiency of power generation, for instance, in an effort to increase the lifespan of the device. For example, in some embodiments, an implantable energy harvester (IEH) interface may be or may be used to supplement the primary power source, for instance, for a rapid top-up of charge of a device power reservoir.

In various embodiments, human energy harvesting sourced from kinetic and thermal energy, for example, using piezoelectric (PEG or PZT) and/or thermoelectric (TEG) generators, respectively, may be used (see, for example, FIGS. 13B-13D). In some embodiments, energy harvesting devices may be configured to generate additional power of, for instance, up to 1 Watt (W). For example, sleeping can produce approximately 81 mW of power, whereas sprinting can produce 1630 mW of power. The human body can also retain (or maintain its) temperature even when the ambient temperature changes. Human energy harvesting can also be supplemented with wireless energy harvesting. A non-limiting example of wireless energy harvesting may include ultrasonic transmission, which converts the energy of surface-applied ultrasound beam to a high-frequency current (for instance, up to 20 nW).

In exemplary embodiments, the control circuitry may communicate using wireless communication. In various embodiments, the wireless communication may be facilitated using at least one of radio frequency (RF), ultra-high frequency (UHF), near field communication (NFC), Bluetooth, Bluetooth Low Energy (Bluetooth LE or BLE), or communications based on the IEEE 802.15 standard. In some embodiments, the adjustment device may include an antenna to receive wireless signals. In various embodiments, the antenna may be arranged on an outer surface of the adjustment device. In certain implantations of an adjustment device, there may be space for an external or protruding (or partially external or protruding) antenna. For example, in typical surgical practice, the top of an LLN is embedded below the top of the tibia. Consequently, there is some space available for a protruding antenna. In some embodiments, the protruding antenna may be formed of biocompatible materials. For example, an antenna wire fabricated from magnesium alloy may be acceptable because magnesium is slowly absorbed by the body without detrimental effects. In another example, an antenna may be affixed to, mounted on or in, embedded on or in, or, at least partially, enclosed within a portion of an LLN, such as a nail cap.

In some embodiments, the motorized drive assembly is stationary. In exemplary embodiments, at least a portion of the motorized drive assembly may travel longitudinally along with distal end. In exemplary embodiments, at least one of a power supply element or the control circuitry, may travel longitudinally with the motorized drive assembly. In various embodiments, at least one of a power supply element or the control circuitry may maintain operable connections via at least one of wired connections, wireless connections, or circuitry as the motorized drive assembly travels longitudinally.

In various embodiments, the motorized drive assembly may include a geared motor. In some embodiments, the motorized drive assembly may include a geared motor with an integrated encoder for positional feedback. In some embodiments, the encoder may include an optical encoder and/or an IR tracking sensor for fine and coarse positional control, respectively.

In various embodiments, the geared motor may include a pinion gear and a spur gear. In exemplary embodiments, the geared motor may include a stepped thrust bearing operative to support axial forces generated by the motor.

In some embodiments, the motorized drive assembly may include a motor that is prevented from axial rotation. In various embodiments, the motor compartment may include a slot operative to receive a corresponding projection on an outer surface of the motor to prevent axial rotation of the motor, for example, during distraction. In some embodiments, the motor compartment may include at least one step to isolate the motor and prevent axial rotation of the motor.

In various embodiments, the motor may operate to rotate a spindle coupled to the drive mechanism via a coupler, thereby causing the drive mechanism to rotate. In some embodiments, the drive mechanism may include a threaded rod. In exemplary embodiments, the motor may rotate in a first direction to cause distraction of a bone of a patient and rotate in a second direction to cause compression of the bone.

In some embodiments, the bone adjustment device may be tailored for weight bearing. In various embodiments, the bone adjustment device may facilitate continuous or semi-continuous actuation. In some embodiments, the motor may be operably coupled to a position sensor, encoder, and/or the like to enable calibrated continuous or semi-continuous actuation. In various embodiments, the position sensor may have sub-millimeter accuracy of at least about $1/1444$ millimeters.

In some embodiments, a limb lengthening nail, configured to be implanted within the intramedullary canal of a bone of a patient, may include a proximal portion configured to attach to a first bone portion on a first side of a cut in the bone, at least a portion of the proximal portion may be or may form an outer housing, a distal portion may be configured to attach to a second bone portion on a second side of the cut, the first side opposite the second side, and a motorized drive assembly may be hermetically sealed within an inner housing arranged within the outer housing. In some embodiments, the motorized drive assembly may include a memory configured to store prescription information, a power management system comprising at least one charging circuit powered via at least one battery, a wireless receiver configured to receive wireless signals transmitting the prescription information from an external computing device, an electric motor operably coupled to rotate a drive shaft engaged with the distal portion to cause movement of the distal portion away from the proximal portion, and an encoder operably coupled to the electric motor, the encoder configured to actuate the electric motor to rotate the drive shaft based on the prescription information.

In some embodiments, the power management system may include or may be operably coupled to an energy harvesting power source or system. As described in more detail below, energy harvesting may operate via temperature differences (e.g., via the thermoelectric effect), mechanical energy harvesting, and/or ultrasonic energy harvesting. In various embodiments, the energy harvesting power source may be operative to, inter alia, enhance the longevity of battery-operated devices, which may, among other things, reduce or even eliminate invasive battery replacement surgery. In some embodiments, the energy harvesting power source may operate to harvest energy based on at least one of body heat of the patient (e.g., thermoelectric energy harvesting) or leg movement of the patient (mechanical energy harvesting).

In various embodiments, the encoder may operate to semi-continuously actuate the electric motor based on the prescription information.

In exemplary embodiments, the wireless communication may include at least one of radio frequency (RF), ultra-high frequency (UHF), near field communication (NFC), Bluetooth, or Bluetooth Low Energy (BLE), an Institute of Electrical and Electronics Engineers (IEEE) 802.11 communication protocol, or an IEEE 802.15 communications protocol. In some embodiments, NFC may be used given that the reader (for instance, a smartphone) can act as the power source for the interaction so that any interaction would be at least power neutral for the implantable bone adjustment device and may also potentially provide for a rapid top-up of charge of the power reservoir.

In various embodiments, the inner housing may include a slot and the motor comprising at least one projection configured to engage the slot to prevent rotation of the motor during rotation of the drive shaft.

In some embodiments, the limb lengthening nail may further include an encoder, such as an optical encoder, and/or a sensor, such as an infrared (TR) sensor, to monitor engagement between the electric motor and the drive shaft.

In various embodiments, an outer diameter of the limb lengthening nail is about 8 to about 10 millimeters. In some embodiments, the limb lengthening nail may be configured as an intramedullary (IM) nail.

In some embodiments, the charging circuit may include a charge pump circuit having at least one capacitor, the charging circuit to provide power to actuate the motorized drive assembly responsive to a threshold amount of voltage being stored on the at least one capacitor.

In exemplary embodiments, the prescription information may include adjustment parameters indicating a length of adjustment over a defined time period. In some embodiments, the wireless receiver may be configured to transmit wireless signals providing status information to the external computing device. In various embodiments, the status information may include an amount of extension of the limb lengthening nail at a defined time period.

In various embodiments, the motorized drive assembly may include a geared motor. In some embodiments, the motorized drive assembly may include a geared motor with an integrated encoder for positional feedback. In some embodiments, the encoder may include an optical encoder and/or an IR tracking sensor for fine and coarse positional control, respectively.

In various embodiments, the geared motor may include a pinion gear and a spur gear. In exemplary embodiments, the geared motor may include a stepped thrust bearing operative to support axial forces generated by the motor.

In some embodiments, the motorized drive assembly may include a motor that is prevented from axial rotation. In various embodiments, the motor compartment may include a slot operative to receive a corresponding projection on an outer surface of the motor to prevent axial rotation of the motor, for example, during distraction. In some embodiments, the motor compartment may include at least one step to isolate the motor and prevent axial rotation of the motor.

In various embodiments, the motor may operate to rotate a spindle coupled to the drive mechanism via a coupler, thereby causing the drive mechanism to rotate. In some embodiments, the drive mechanism may include a threaded rod.

In some embodiments, the limb lengthening nail may be tailored for weight bearing. In various embodiments, the limb lengthening nail may be tailored for weight bearing by setting a duty cycle in the pulsed driver circuit that attempts to adjust the nail. In this situation, switching to a duty cycle from an adjustment once every minute to once every 45 seconds would increase the number of adjustment intervals from 1440 to 1920 adjustment intervals per day respectively. A 33% increase in adjustment intervals could accommodate any attempt made by the software to adjust the frame during very high loading periods, thereby allowing the device to skip and make adjustments at the next interval. This type of duty cycle would ensure that adjustments were only attempted when the applied forces are light, while still maintaining a more fractionated rhythm for bone adjustment.

In various embodiments, the limb lengthening nail may facilitate continuous or semi-continuous actuation. In some embodiments, the motor may be operably coupled to a position sensor to enable calibrated continuous or semi-continuous actuation. In various embodiments, the position sensor may have sub-millimeter accuracy of at least about $1/1444$ millimeters.

In one embodiment, a method for adjusting a hone of a patient may include implanting a limb lengthening nail in the bone of the patient, in which the limb lengthening nail may include a proximal portion configured to attach to a first bone portion on a first side of a cut in the bone, at least a portion of the proximal portion foil ting an outer housing, a distal portion configured to attach to a second bone portion on a second side of the cut, the first side opposite the second side, and a motorized drive assembly hermetically sealed within an inner housing arranged within the outer housing. In some embodiments, the motorized drive assembly may include a memory configured to store prescription information, a power management system comprising at least one charging circuit powered via at least one battery, a wireless receiver configured to receive wireless signals transmitting the prescription information from an external computing device, an electric geared motor operably coupled to rotate a drive shaft engaged with the distal portion to cause movement of the distal portion away from the proximal portion, and an encoder operably coupled to the electric motor, the encoder configured to actuate the electric motor to rotate the drive shaft based on the prescription information, and providing control instructions to the limb lengthening nail using an external computing device.

Embodiments of the present disclosure provide numerous technological advantages and technical features over conventional systems. For example, one non-limiting technological advantage may include providing an implantable bone adjustment device operating using a hermetically encapsulated electric motor that requires lower energy and can be controlled with increased precision than available using conventional devices. In another example, a non-limiting technological advantage may include providing an implantable bone adjustment device that is full or substantially full weight bearing for the patient (distraction may benefit from occurring during weight bearing to provide semi-continuous actuation (for instance, 1440 actuation steps per day) (in one non-limiting example, using pulsed DC motor speed control, motor-On (7 ms), motor off (993 ms), motor on (7 ms), and so on). In another example, a non-limiting technological advantage may include providing an implantable bone adjustment device with an electric motor that may be powered, at least in part, based on energy harvesting techniques, including, temperature differences (e.g., via the thermoelectric effect), mechanical energy harvesting, and/or ultrasonic energy harvesting.

In a further example, a non-limiting technological advantage may include providing an implantable bone adjustment device configured for continuous or semi-continuous actuation that may be monitored with high accuracy on a constant or continuous basis. In an additional example, a non-limiting technological advantage may include providing an implantable bone adjustment device configured that may be used for both lengthening (distraction) and compression. In another example, a non-limiting technological advantage may include providing an implantable bone adjustment device with an electronic motor that may be arranged within smaller form factors than available via conventional devices, including an 8, 9, or 11 millimeter diameter LLN.

In an additional example, a non-limiting technological advantage may include providing an implantable bone adjustment device with an on-board battery, charging circuit and/or energy harvesting device, eliminating the need for an implantable magnet or sub-dermally implanted (radio-frequency (RF)) receiver connected to the nail by a wire. In a further example, a non-limiting technological advantage may include providing an implantable hone adjustment device having a control system configured to wirelessly receive control signals, including uploading prescription plans for operating the implantable bone adjustment device and transmit and receive basic commands from the implantable bone adjustment device, such as extension rate, an extension direction, a total extension, a battery level, and/or the like. In another example, a non-limiting technological advantage may include providing an implantable bone adjustment device that may be controlled via a standard computing device (e.g., smart phone, tablet, personal computer, and/or the like) that does not require a specialized control device, such as an external magnetic control device, hand-held RF transmitter, and/or the like. In this instance, the implantable bone adjustment device (for instance, an LLN) can interact with a smartphone or other computing device to report on an adjustment or companion application the performance of the implantable bone adjustment device and its functionality and to receive commands as necessary.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed methods, systems, and apparatuses will now be described, with reference to the accompanying drawings, in which:

FIGS. 3A-3C depict an example embodiment of an implantable bone adjustment device in accordance with one or more features of the present disclosure;

FIG. 4 depicts a first example embodiment of a drive assembly of an implantable bone adjustment device in accordance with one or more features of the present disclosure;

FIG. 6 depicts an example embodiment of an enclosure system for hermetically sealing a drive assembly of an implantable bone adjustment device in accordance with one or more features of the present disclosure;

FIG. 12 depicts an example embodiment of control circuitry of an implantable bone adjustment device in accordance with one or more features of the present disclosure;

FIGS. 15A and 15B depict example embodiments of graphical user interfaces (GUIs) for a bone adjustment application for controlling functions of an implantable bone adjustment device in accordance with one or more features of the present disclosure;

Figure 1:
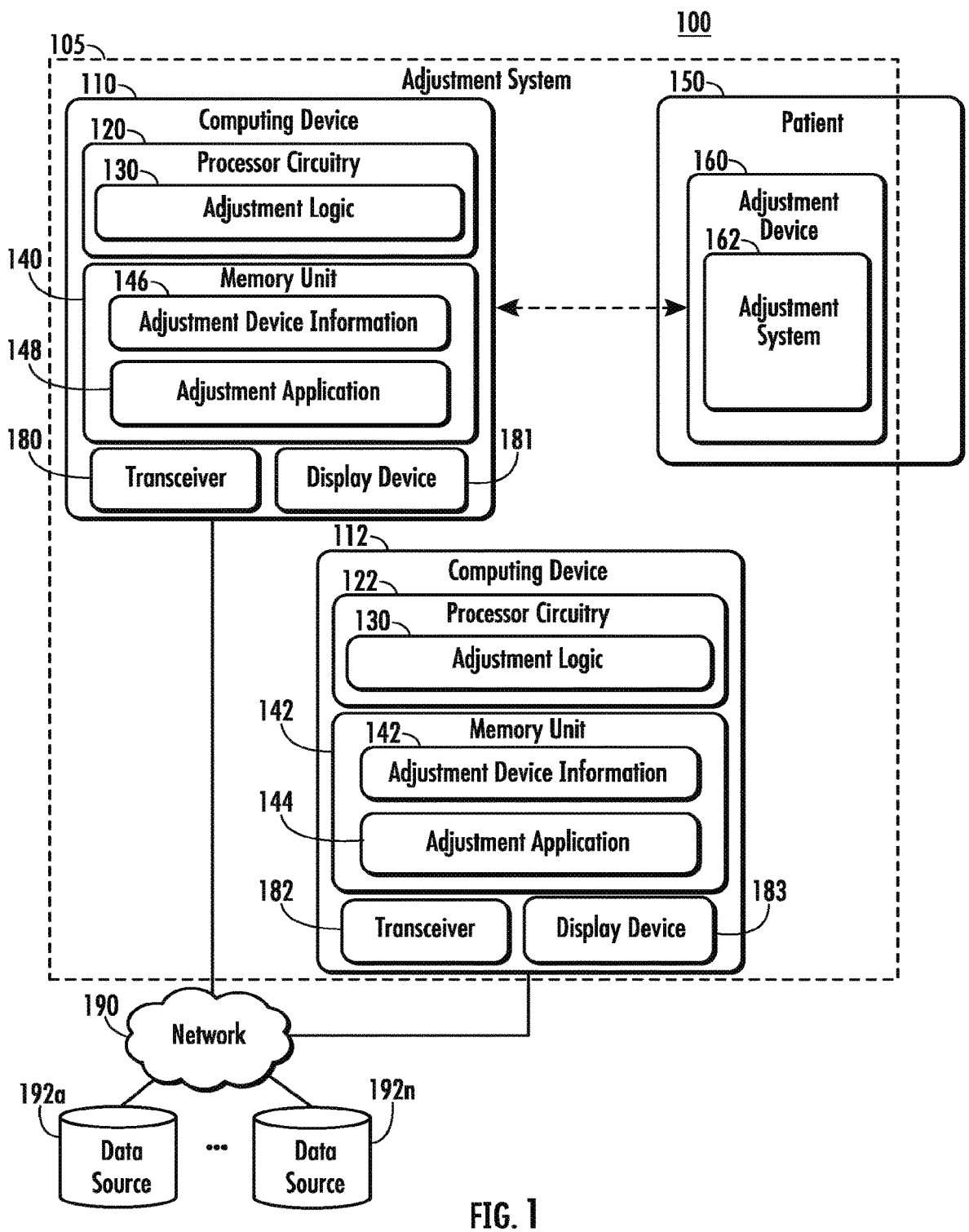
FIG. 1 depicts an example embodiment of an operating environment for an implantable bone adjustment device in accordance with one or more features of the present disclosure.

The drawings are not necessarily to scale. The drawings are merely representations, not intended to portray specific parameters of the disclosure. The drawings are intended to depict example embodiments of the disclosure, and therefore are not to be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

Various features or the like of an implantable bone adjustment device will now be described more fully hereinafter with reference to the accompanying drawings, in which one or more features of the implantable bone adjustment device will be shown and described. It should be appreciated that the various features may be used independently of, or in combination, with each other. It will be appreciated that an implantable bone adjustment device as disclosed herein may be embodied in many different forms and should not be construed as being limited to the embodiments set forth herein. Rather, these embodiments are provided so that this disclosure will convey certain features of the implantable bone adjustment device to those skilled in the art.

As will be described herein, in accordance with one or more features of the present disclosure, an implantable bone adjustment device is disclosed. In one embodiment, as will be appreciated by one of ordinary skill, the implantable bone adjustment device may be or may include an orthopedic distraction device. In various embodiments, the implantable bone adjustment device may be in the form of a nail, such as a limb adjustment nail. In some embodiments, the implantable bone adjustment device may be configured as a limb lengthening nail (LLN) operative to provide distraction (lengthening) forces and/or compression forces on a portion of a bone of a patient. In various embodiments, the implantable bone adjustment device may be configured as a nail operative to be implanted within the intramedullary canal (IM) of a bone of a patient. Although an LLN configured for implantation within an IM canal are used in examples in the present disclosure, embodiments are not so limited, as implantable bone adjustment devices may be configured to provide compressive, rotational, or other types of forces and/or may be implanted on an external surface of the bone of the patient. In one particular example, an LLN configured according to some embodiments may also be used as an improved high tibial osteotomy implant system, for example, to treat unicompartmental knee osteoarthritis (OA) by offering finer adjustment optimized post-op alignment and reduced soft tissue irritation compared to standard treatments and devices.

In some embodiments, the implantable bone adjustment device may include an electric motor configured to drive at least one portion of the bone adjustment device. The electric motor may be hermetically sealed within a housing or other portion of the implantable bone adjustment device. In various embodiments, the electric motor may include a gear and/or drive shaft mechanism (e.g., a screw or "lead screw") operative to convert the rotation of the motor into an axial movement with high force (for instance, greater than 900 Newtons (N)-2000 N). In various embodiments, the electric motor may be capable of a peak static equilibrating load of 2000 N (for instance, attained at the end of lengthening). In some embodiments, the electric motor may be controlled with high accuracy (for instance, millimeter or sub-millimeter accuracy), which may enable continuous or semi-continuous actuation. In various embodiments, the electric motor may be configured to turn in both directions, allowing lengthening and compression. In some embodiments, for example, the lead screw may be coupled with a (miniature) DC motor operative to drive the linear motion of the distractor housing or tube. The drive system may be configured to have sufficient motor power and torque, which will produce sufficient axial force to extend the bone sections against the axial resistance of the muscles.

In some embodiments, the implantable bone adjustment device (for example, a LLN) may be actuated by a miniature drive system, that may be composed of a motor (for example, a micromotor, a DC motor, a DC micromotor, and/or the like), a gearhead (for example, a planetary gearhead), and/or an encoder (for example, an incremental encoder). Various considerations may be applied to select drive system components. Two non-limiting example criteria may include the outer diameter of the drive system and the torque output at the gearhead. Since the overall system is implanted into the intramedullary canal of the bone, the drive, design considerations are to use a system that is as small as possible. On the other hand, the drive system must provide the torque required to overcome the axial loads exerted during the lengthening process. In some embodiments, these requirements may lead to the selection of a miniature DC motor drive system with an outer diameter of about 8 mm. In some embodiments, the motor may be coupled with a gearhead, for example, that has a reduction as high as about 4096:1. In exemplary embodiments, an incremental encoder may also be mounted to the motor-gearhead assembly, for example, to measure the angular velocity and position information. In some embodiments, the encoder may be mounted to the rear end of the motor.

In exemplary embodiments, the electric motor may be powered with internal components, such as via batteries and/or a charging circuit to regulate the power consumption of the motor, encoder, and/or communication (for instance, BLE) modules (see, for example, FIGS. 13A-13D). For example, power required for a distraction process may be supplied by one or more 3 volt (V) lithium ion coin cell batteries, which may be supplemented with a charging circuit and/or energy harvesting device. For example, 2-4 coin cell batteries may be used depending on power requirements, dimensions of the battery, and/or capacity (for instance, to achieve a target of about 90 milliamp hours and about 3 volts). The battery can also be set to "shelf-mode" using a companion or adjustment application, for example, whereby the current is set to about 1.5 to about 2 µA, which translates to a shelf-life in excess of 35,000 hours (4 years) assuming 70,000 µAh.

In some embodiments, additional electric power (for instance, up to 100 µW) may be provided via embedding a thermoelectric generator (TEG) (see, for example, FIG. 13C) in the implantable bone adjustment device during distraction from "inside the body." In this manner, some embodiments may provide direct utilization of the temperature difference intrinsically existing throughout the whole biological body. The TEG module combined with a low-power synchronous (DC/DC) boost converter, which may be capable of boosting 10 mV input voltage to 1 V output voltage, may help to stabilize the energy output and/or improve the voltage output. Due to the low-temperature difference between the trunk of the body (36.9° C.) and the surface of the skin (33° C.), the TEG may use an optimized number of thermopiles to achieve enough energy production. These thermophile chips (for example, 4 mm×4 mm) may contain over 4000 thermocouples connected electrically in series. This is type of harvester may deliver up to 10 µW power with a minimum temperature gradient of 1-degree.

Alternatively, a kinetic (or mechanical) energy harvester can be used to siphon energy from patient movements, outside of the body of the device, and can be embedded within the implantable bone adjustment device. This type of energy harvester uses a piezoelectric material that can convert leg motion during walking or any other activity into electrical energy. A non-limiting example of a piezoelectric material may include zirconate titanate. The PZT material may operate as one or more sensors to detect deflection of the implant and/or to provide stable power for the functional circuit. Therefore, the output power of the PZT varies with the force applied on the implantable bone adjustment device. The integrated power management circuit for a piezoelectricity converter may be or may include a multilayer piezoelectric element made from this material with dimensions of 5 mm diameter and 2.5 mm height, which can be housed inside the cannulation and can produce an average power output up to 10 µW. The multilayer piezoelectric element may have various shapes, such as being ring-shaped.

In some embodiments, a power circuit including the SC converter (switching capacitor based on DC-DC converter) and/or low drop-out voltage regulator (LDO) may be used for the monitoring system of the implantable bone adjustment device, making the system self-powering. The output signal of the PZT may be first rectified, for instance, by a full-wave bridge rectifier, to convert the bipolar piezoelectric output to a unipolar signal. It is then followed by a storage circuit, which may be or may include a capacitor in parallel with the load circuit. An oscillator circuit may be used to generate clock for an SC converter, for example, to lower the input voltage from ~10 V to 2 V. The input voltage may be controlled by programmable switches (for instance, four programmable switches) and the LDO may operate to drop the voltage further to a steady voltage.

In some embodiments, position or positional control of a component moved by the electric motor may be achieved using an encoder and/or sensor operably coupled to the electric motor. A non-limiting example of an encoder may include an optical encoder or an incremental encoder, including, for instance, an electrically adapted optical incremental encoder. The incremental rotary encoder can be adapted to function as an absolute encoder electronically so that its status can be logged directly into system memory, such as a non-volatile memory, continuously. In various embodiments, a sensor may include an infrared sensor, such as an infrared line tracking sensor and/or the like. In some embodiments, the encoders or sensors may be used to verify operation of parts of electric motor, such as verifying that there is no (or monitoring an amount of) slippage between the motor spindle and the drive element (or lead screw). In various embodiments, the encoders and/or sensors may monitor for proper operation of the electric motor and/or components thereof, such as monitoring that the bone adjustment device is extending/compressing in the proper direction.

In various embodiments, the electronic motor may be controlled via wireless communication, such as radio frequency (RF) signals, ultra-high frequency (UHF) signals, near field communication (NFC), Bluetooth, Bluetooth Low Energy (Bluetooth LE or BLE), communications based on the IEEE 802.15 standard, and/or the like. In some embodiments, the implantable bone adjustment device may include a controller, micro-controller, control unit, circuitry, memory, and/or other logic elements for controlling operational features of the electric motor. The controller may receive/transmit wireless signals from/to a computing device. For example, the controller may receive control signals for features of the implantable bone adjustment device to perform certain functions, such as actuate the electric motor to extend a portion of the implantable bone adjustment device. In another example, the controller may transmit status information (such as motor position, extension length, and/or the like) to the computing device.

FIG. 1 illustrates an example of an operating environment 100 that may be representative of some embodiments. As shown in FIG. 1, operating environment 100 may include a bone adjustment system 105. In various embodiments, bone adjustment system 105 may include computing device 110 and/or 112 communicatively coupled to network 190 via a transceiver or other communication interface 180. Computing devices 110 and/or 112 may be or may include one or more logic devices, including, without limitation, a server computer, a client computing device, a personal computer (PC), a workstation, a laptop, a notebook computer, a smart phone, a tablet computing device, and/or the like. Embodiments are not limited in this context.

As shown in FIG. 1, adjustment system 105 may include an implantable bone adjustment device (or "adjustment device") 160 implanted within a patient 150. In some embodiments, adjustment device 160 may include an LLN device (see, for example, FIGS. 2, 3A, and 3B). In various embodiments, adjustment device 160 may be implanted within an IM canal of a bone of patient 150, such as a femur or tibia.

Adjustment device 160 may include an adjustment system 162 operative to facilitate control, movement, and/or the like of portions of adjustment device 160 to implement an adjustment process, such as bone lengthening. In some embodiments, adjustment system 162 may be or may include an electric motor and associated control, power, and/or communication components (see, for example, FIGS. 4, 5A, 5B, 6, 7A-7C, 8A, and 8B). In various embodiments, adjustment system 160 may include sensors, gauges, or other elements operative to provide status information for adjustment device 160 and/or adjustment system 162. For example, adjustment system 162 may be configured to detect, measure, or otherwise determine operational information (for example, adjustment device information 146) associated with adjustment device 160. Non-limiting examples of sensors may include pressure or force sensors, strain gauge, piezoelectric sensor, Surface Acoustic Wave (SAW) strain sensor, distance sensor (for instance, to measure or determine a distance of travel of a portion of adjustment device), encoders, and/or the like.

Figure 2:
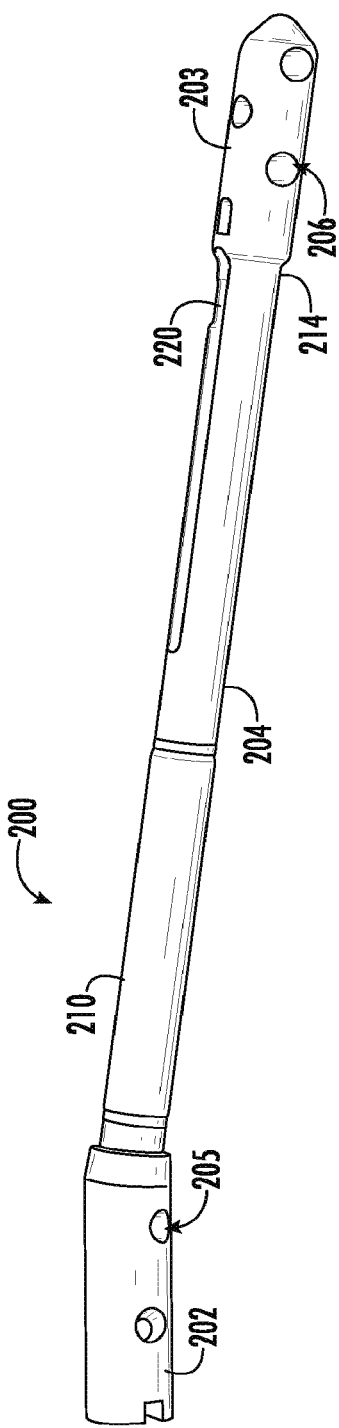
FIG. 2 depicts an example embodiment of an implantable bone adjustment device in accordance with one or more features of the present disclosure.

Referring to FIG. 2, therein is depicted an example embodiment of an implantable bone adjustment device in accordance with one or more features of the present disclosure. As shown in FIG. 2, an adjustment device 200 may be in the form of an LLN having a proximal (or first) portion 202, with a hollow middle section 202, and a distal (or second) portion 203. The distal portion 203 is dimensioned to move within at least a portion of the hollow middle section 202, for example, in a telescoping manner. A drive mechanism or assembly (not shown; see FIGS. 3A, 3B, 4, 5A, 5B, and 6) may be arranged within a drive compartment 210 of middle section 202. The drive assembly may be configured to engage a drive element 220, such as a threaded rod, to cause movement of distal portion 203, for example, in a direction away from proximal portion 202.

In some embodiments, compartment 210 may be a hermetically sealed compartment. In various embodiments, compartment 210 may have a water-tight and/or gas-tight seal. In various embodiments, compartment 210 may have dimensions of about 54 millimeters (mm) long, about a 9 mm outer diameter, and an about 8 mm inner diameter. In some embodiments, compartment may have a length of about 20 mm to about 80 mm, an outer diameter of about 6 mm to about 15 mm, and an inner diameter of about 4 mm to about 12 mm.

Middle section 204 of proximal portion 202 may be at least partially hollow, for example, forming an internal cylindrical chamber, for accommodating a portion of the distal body portion 203, which extends through a distal end 214 of proximal body portion 202. Proximal and distal body portions 202, 203 are dimensioned such that proximal and distal body portions 202,203 can move (or telescope) in both axial directions with respect to one another.

A limb adjustment process using an adjustment device according to some embodiments (such as adjustment device 200) may generally apply Ilizarov's principle of tension-stress, wherein living tissue subjected to slow, steady tension becomes metabolically activated. For example, a bone gap or cut is formed in the bone to be adjusted creating two portions of bone on either side of the cut. A callus is formed at the site of the cut. Subsequent distraction of the gap by forcing the bone portions apart may cause new bone to form to generate an increase in length.

In some embodiments, proximal portion 202 may be affixed to a first portion of bone on a first side of the cut, for example, via fasteners (for instance, screws) threaded or otherwise positioned through fastener openings 205. Distal portion 203 may be affixed to a second portion of bone on a second side of the cut via fasteners threaded or otherwise positioned through fastener openings 206. The drive assembly may operate to actuate threaded rod 220 to cause distal portion 203 to separate from proximal portion 202 to move the second bone portion away from the first bone portion, thereby promoting bone growth.

Figure 3C:
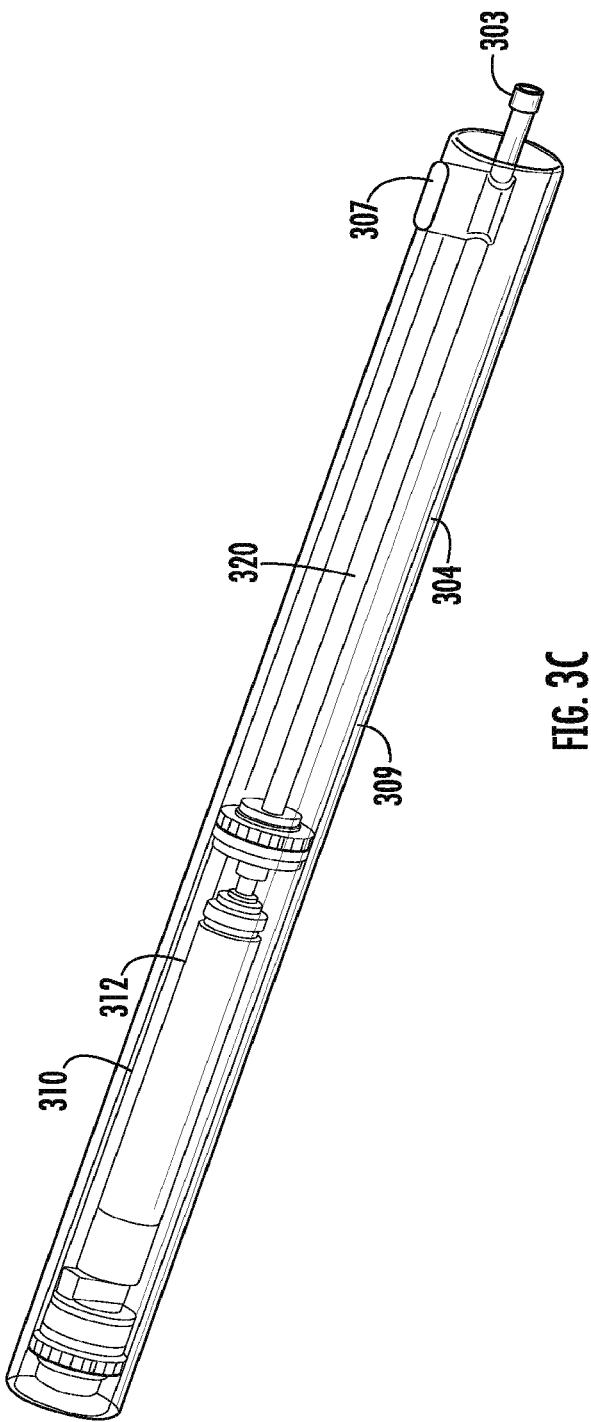

FIGS. 3A-3C depict an example embodiment of an implantable bone adjustment device in accordance with one or more features of the present disclosure. As shown in FIG. 3A, an adjustment device 300 may include a distal portion 303 slidably arranged at least partially within a hollow housing 310 of a middle section 304 of a proximal portion 302. Although FIGS. 3A and 3B depict distal portion 303 as being arranged with proximal portion 302, embodiments are not so limited, for example, in various embodiments, proximal portion 302 may be arranged at least partially within a hollow section of distal portion 303.

In various embodiments, middle section 304 may include a hollow, cylindrical outer housing or tube 309 and an inner housing or tube 310. In some embodiments, outer housing 309 may be configured to cover and protect internal telescopic parts. Outer housing 309 may be integrated with or affixed, for instance, via welding, to a first end 313 (for example, an end configured to be affixed to the bone of the patient) of proximal portion 302. In exemplary embodiments, outer housing 309 may be welded or otherwise engaged with a stopper 307 to prevent translation, rotation, or other unwanted movement. In various embodiments, inner housing 310 may be configured to house a drive assembly 312. For example, inner housing 310 may be hermetically sealed to protect portions of drive assembly 312.

In some embodiments, portions of adjustment device 300, such as proximal portion 302, distal portion 303, housing 309, and/or housing 310 may be formed of rigid, biocompatible materials, such as cobalt chrome. In various embodiments, adjustment device 300 may be used for both left and right anatomy (for instance, a left femur and a right femur), for example, because the adjustment device is not bowed or otherwise formed for one side or another of patient anatomy. In some embodiments, adjustment device 300 may have a diameter of about 8 millimeters to about 11 millimeters. In various embodiments, adjustment device may have a length of up to about 23 centimeters (cm) and distal end 203 may be configured to travel about 5 cm at full extension.

In some embodiments, drive assembly 312 may include a motor 330, such as an electronic, battery-powered motor. In various embodiments, motor 330 may include a fully integrated motor configured to fit within 8, 9 and 11 mm nails using 6 and 8 mm diameter motors.

Referring to FIGS. 3B and 3C, FIG. 3B depicts area 311 of FIG. 3A and FIG. 3C depicts a perspective view of middle section 304. As shown in FIGS. 3B and 3C, a threaded rod 320 may be attached to distal end 303 via a block 324 and an opposing end of threaded rod 320 may be attached to drive assembly 312. In some embodiments, block 324 may have an internal, threaded bore (not shown). In various embodiments, the bore of block 324 may be dimensioned to permit passage of threaded rod 320 therethrough. In some embodiments, threaded rod 320 may extend through stopper 307, which may be stationary and formed as a fastener or nut for threaded rod 320 to extend through. Outer housing 309 may be affixed (for example, welded) to a portion of stopper 307 (and to the end of proximal portion 302) to prevent translation or other unwanted movement of outer housing 309 or proximal portion 302. Rotation of motor 330 in one direction may cause distraction, and rotation of motor in the opposite direction may cause compression.

In some embodiments, drive assembly 312 and/or components thereof, such as motor 330, may be longitudinally stationary. For example, drive assembly 312 may not travel as distal portion 303 moves away from proximal portion 302. In other embodiments, drive assembly 312 and/or components thereof, such as motor 330, may be move longitudinally along with distal end 303 during distraction (and in the opposite direction during compression). In an embodiment in which drive assembly 312 and/or components thereof, such as motor 330, moves longitudinally along with distal end 303 during distraction, drive assembly 312 may be configured such that motor 330 remains operably coupled to power supplies, energy harvesters, sensors, control circuitry, and/or the like to maintain operational features. In one example, some or all of power supplies, sensors, control circuitry, and/or the like may travel along with motor 330. In another example, some or all of power supplies, energy harvesters, sensors, control circuitry, and/or the like may maintain operable connections via wired connections, wireless connections, circuitry (e.g., via a PCB board), shape-memory materials, and/or the like.

Referring to FIG. 1, computing devices 110 and/or 112 may be configured to manage, among other things, operational features of adjustment device 160.

Computing devices 110 and/or 112 may include a processor circuitry 120 and/or 122 that may include and/or may access various logics for performing processes according to some embodiments. For instance, processor circuitries 120 and/or 122 may include and/or may access an adjustment logic 130. Processing circuitries 120 and/or 122, adjustment logic 130, and/or portions thereof may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, a proportional-integral-derivative (PID) controller, FG circuitry, variations thereof, combinations of any of the foregoing, and/or the like.

Although adjustment logic 130 is depicted in FIG. 1 as being within processor circuitries 120 and 122, embodiments are not so limited. For example, adjustment logic 130 and/or any component thereof may be located within an accelerator, a processor core, an interface, an individual processor die, implemented entirely as a software application (for instance, an adjustment application 148) and/or the like. In some embodiments, adjustment logic 130 may include logic operative to perform adjustment processes, including controlling operational features of adjustment system 162. In various embodiments, adjustment logic 130 may include instructions of adjustment application (companion application or companion "app") 148 being executed via processor circuitries 120 and/or 122.

Memory units 140 and/or 142 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory units 140 and/or 142 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory units 140 and/or 142 may store various types of information and/or applications for an adjustment process using adjustment device 160 according to some embodiments. For example, memory units 140 and/or 142 may store adjustment device information 146 and/or an adjustment application 148. In various embodiments, some or all of adjustment device information 146 and/or adjustment application 148 may be stored in one or more data sources 192*a-n* accessible to computing devices 110 and/or 112 via network 190.

In some embodiments, adjustment information 146 may include any information associated with adjustment device 160, adjustment system 162, statuses thereof, and/or operational features thereof. For example, adjustment information 146 may include operating parameters, extension information (for instance, extension state or distance of distal end 303), pressure or force information (for instance, the amount of force being imparted on a portion of bone by distal end 203), power information, battery information, error information, prescription information, and/or the like. In various embodiments, adjustment application 148 (or companion application or "app") may include a software application operative to provide a user interface (see, for example, FIGS. 15A and 15B) and/or control functions for adjustment system 162 (for instance, a control feature to cause actuation of drive assembly 312 to move distal end 303). Embodiments are not limited in this context.

In some embodiments, computing device 110 may be configured as a local or central control device for managing adjustment device 160 via adjustment system 162. For example, computing device 110 may be a computing device, such as a smart phone, tablet computing device, personal computer (PC), and/or the like associated with patient 150 or a healthcare professional. Computing device 110 may be communicatively coupled to adjustment system 162 via one or more communication protocols, such as RF, NFC, Bluetooth, BLE, and/or the like. In various embodiments, computing device 110 may be used by patient 150 or a healthcare professional to control operational features of adjustment system 162, such as activating a drive assembly to move a portion of adjustment device 160, upload a prescription to adjustment system 162, and/or the like.

In some embodiments, computing device 112 may be or may include a healthcare provider or adjustment device manufacturer server, cloud computing system, or other platform. In various embodiments, computing device 112 may be communicatively coupled to computing device 110, for example, via network 190. Computing device 112 may be configured to transmit information to computing device 110, such as a prescription or other adjustment information. Computing device 112 may operate to receive information from computing device 110, such as adjustment information 146. In some embodiments, computing device 112 may operate to communicate directly with adjustment system 162. In other embodiments, computing device 112 may communicate with adjustment system 162 via computing device 110. For example, computing device 112, for instance, via adjustment application 148, may transmit a prescription (or other adjustment instruction) to adjustment application 148 operating on computing device 110. Computing device 110 may transmit the prescription (or adjustment instruction) to adjustment system 164, for example, to cause actuation of drive assembly 312.

For example, computing device 112 may scan for adjustment system 162 (for instance, polling at a time interval, such as every 15 minutes). Computing device 112 may establish a connection with adjustment system 162, for instance, via computing device 110 to receive updates, status, and/or the like and/or to transmit control instructions, including prescriptions, to computing device 110 and/or adjustment system 162. Embodiments are not limited in this context.

FIG. 4 depicts a first example embodiment of a drive assembly of an implantable bone adjustment device in accordance with one or more features of the present disclosure. As shown in FIG. 4, a drive assembly 412 may include a motor 430. In some embodiments, motor 430 may be or may include a geared motor (see, for example, FIGS. 5A, 5B, and 6). In various embodiments, motor 430 may be powered by a battery power source 436 alone or in combination with a charging circuit 434. In some embodiments, charging circuit 434 may be or may include a capacitor circuit (see, for example, FIG. 13). In exemplary embodiments, battery power source may include at least one coin cell battery, such as a lithium ion battery (for instance, a 3 volt, 3.6 volt, 3.7 volt, or 4.2 volt lithium ion battery cell). Drive assembly 412 may include a control system 432, for example, embodied as a PCB board with surface-mount components. In some embodiments, motor 430 may include or may be associated with an encoder to provide speed and/or position control signals. For example, motor 430 may be controlled, at least in part, via an optical encoder or transducer.

In various embodiments, drive assembly 412 may be arranged within an assembly housing 414. In some embodiments, assembly housing 414 may be configured to hermetically seal drive assembly 430. In exemplary embodiments, assembly housing 414 may be arranged within an outer housing (see, for example, outer housing 309 of FIG. 3).

In some embodiments, motor 430 may be operably coupled to a threaded rod 420. Actuation of motor 430 may cause rotation of threaded rod 420, which may cause a distal end (for instance, distal end 203 or 303) to move away from a proximal end (for instance, proximal end 202 or 302) of an adjustment device.

Figure 5A:
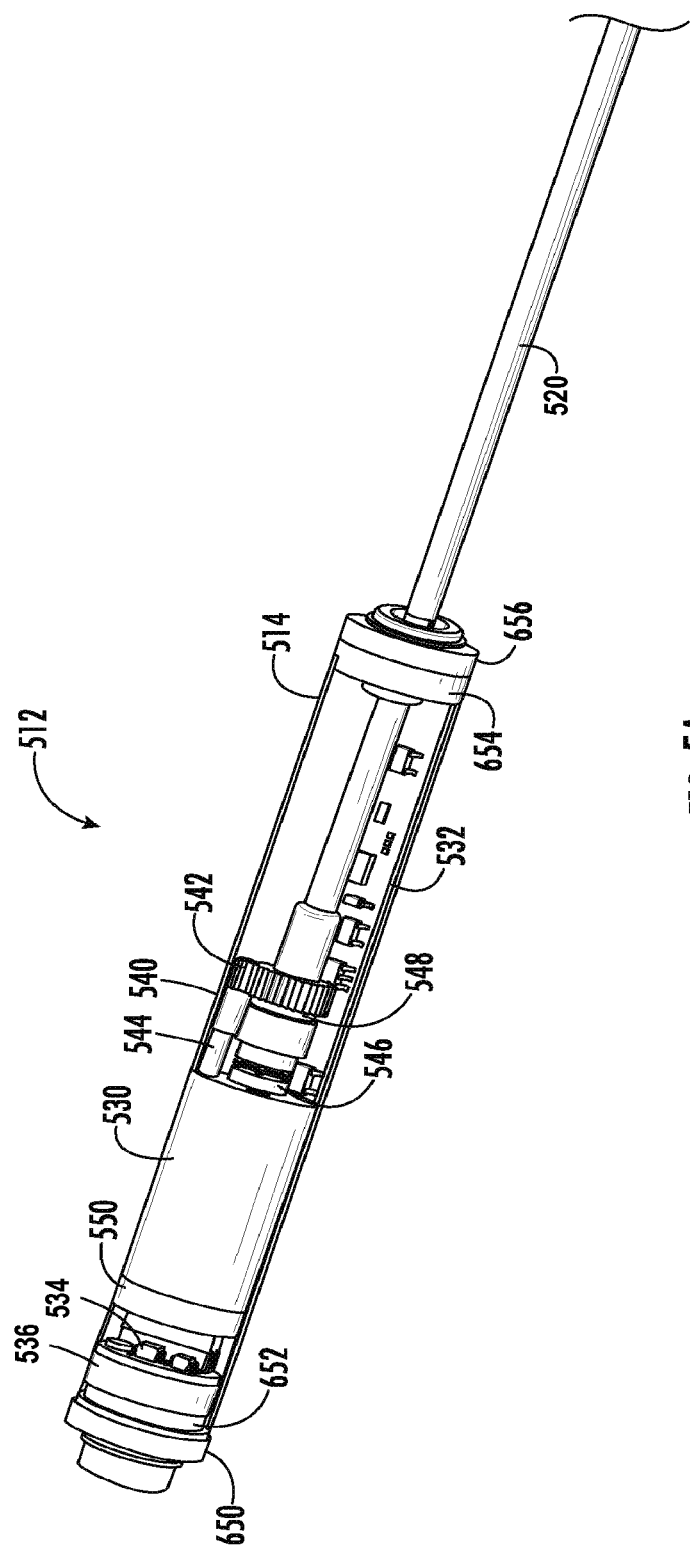
FIGS. 5A and 5B depict a second example embodiment of a drive assembly of an implantable bone adjustment device in accordance with one or more features of the present disclosure.
Figure 5B:
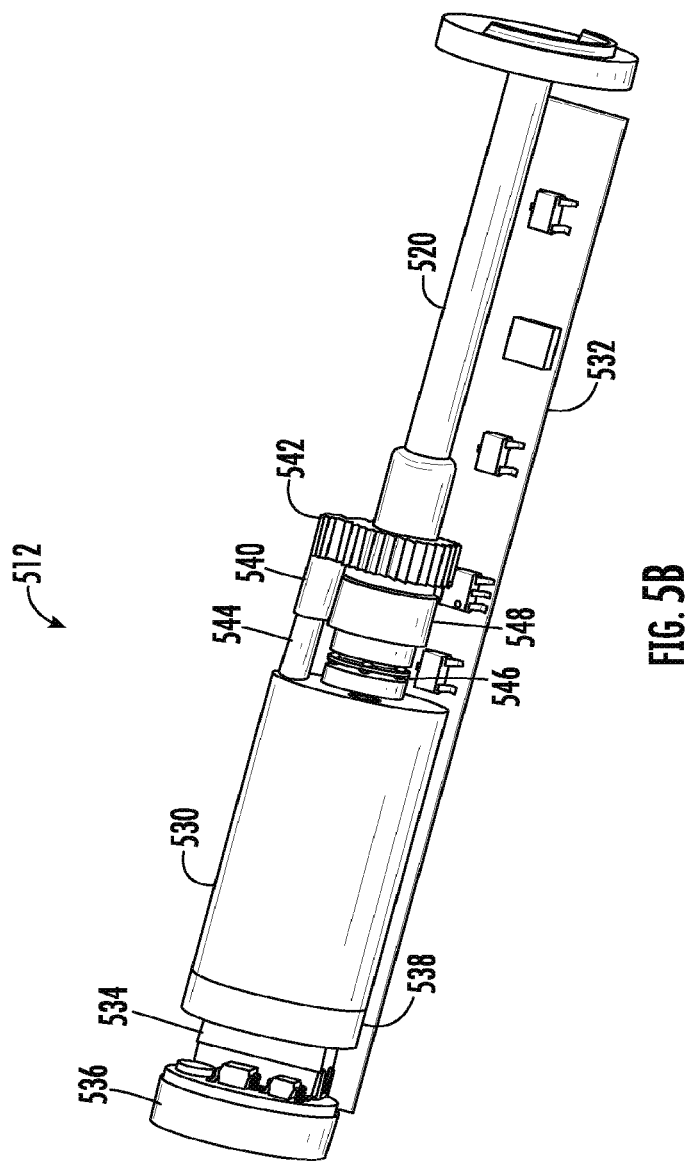

FIGS. 5A and 5B depict a second example embodiment of a drive assembly of an implantable bone adjustment device in accordance with one or more features of the present disclosure. More specifically, FIGS. 5A and 5B depict a perspective view of a drive assembly 512 depicted with and without an assembly housing 514, respectively. In some embodiments, drive assembly 512 may include a geared motor 530 with an integrated encoder 550. Motor 530 may be associated with control circuitry 532, charging circuit 534, and battery power source 536.

Actuation of motor 530 may cause rotation of at least one pinion gear 540 arranged on a spindle and configured to engage spur gear 542 to cause axial rotation of spur gear 542. In some embodiments, drive assembly 512 may include various components operably engaged with motor 530 and/or gears 540, 542 to facilitate motor functionality, such as managing forces generated by actuation of motor 530 and/or rotation of threaded rod 520. For example, a thrust bearing 546 may be used, among other things, to support an axial load on a rotating threaded rod 520. In various embodiments, thrust bearing 546 may be a step thrust bearing associated with at least one step. In some embodiments, spur gear 542 may have a supplementary spur gear ratio, for example, of 2.78:1. The supplementary gear ratio may have different values according to various embodiments, such as 2:1, 2.5:1, 3:1, 3.5:1, 4:1, and any value or range between any two of these values. In various embodiments, thrust bearing 546 at the base of a lead screw (for instance, drive element 520) may be used to support the high axial forces experienced by adjustment device and/or components thereof (for instance, motor 530). In some embodiments, thrust bearing can withstand loads of up to 912 N or greater and may operate to protect a reducing gearbox, which typically have delicate components that cannot withstand forces of high magnitude.

FIG. 6 depicts an example embodiment of an enclosure system for hermetically sealing a drive assembly of an implantable bone adjustment device in accordance with one or more features of the present disclosure. More specifically, FIG. 6 depicts an exploded view of an enclosure system 605 for drive assembly 512 of FIGS. 5A and 5B. As shown in FIG. 6, enclosure system 605 may include a protective outer housing or tubing 514 with a grommet or seal arranged at ends of the enclosure, such as a proximal seal 650 and a distal seal 654 (see also, FIG. 5A for a view of an installed enclosure system). In some embodiments, seals 650 and 654 may be used in combination with O-rings 652 and 656, respectively. In various embodiments, seals 650 and 654 and O-rings 652 and 656 may be made of various materials used to form hermetic seals, including, without limitation, rubber, silicone, polymers, combinations thereof, and/or the like. Seals 650 and 654 may be arranged between threaded rod 520 and housing 514 to prevent, among other things, biological materials from getting into housing 514 and contaminating control system 532.

In some embodiments, enclosure system 605 may hermetically seal components of drive assembly 530, for example in a water-tight, fluid-tight, and/or gas-tight enclosure. For example, enclosure 605 may be configured to achieve at least an IPX7 waterproof (or equivalent) rating. In various embodiments, electrical components of drive assembly 530, such as memory and circuitry components of control system 532 may be potted in a soft encapsulant (for instance, a "glop top") using materials such as silicone, polyurethane, combinations thereof, and/or the like to provide additional protection to the electronic components from moisture ingress.

FIGS. 7A-7D depict an example anti-rotation motorized drive assembly of an implantable bone adjustment device in accordance with one or more features of the present disclosure. In some embodiments, operation of a drive assembly may be configured to prevent rotation of motor and/or other components. For example, axial rotation may only be facilitated for gears forced (directly or indirectly) by actuation of the motor and the threaded rod.

Figure 7A:
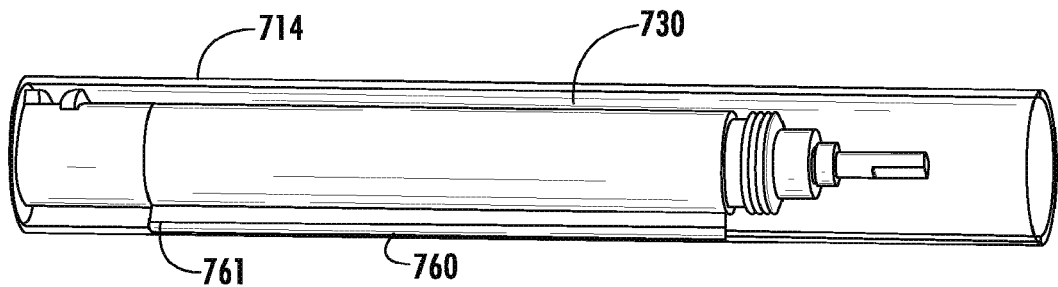
FIGS. 7A-7D depict an example anti-rotation motorized drive assembly of an implantable bone adjustment device in accordance with one or more features of the present disclosure.
Figure 7B:
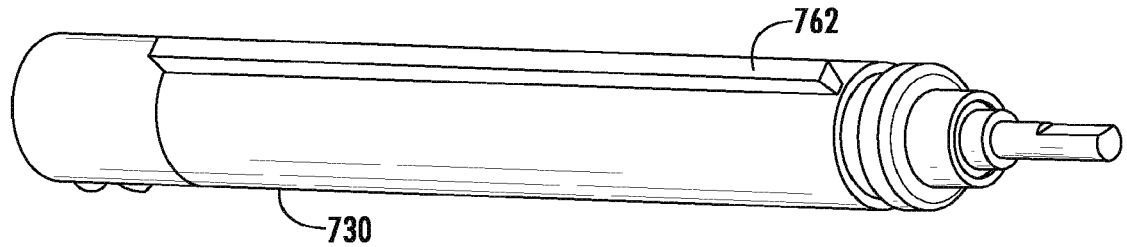
Figure 7C:
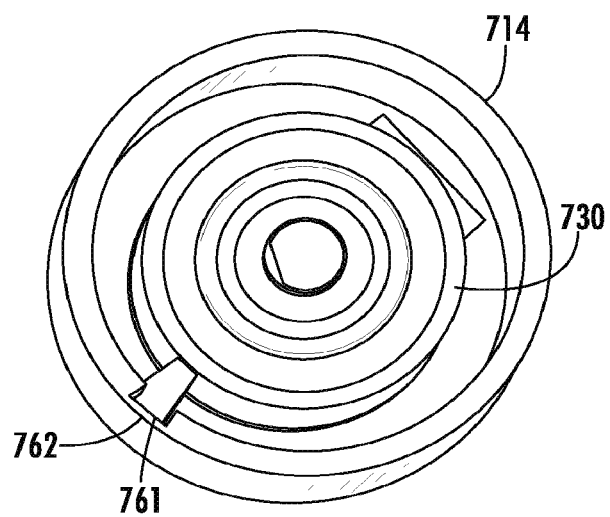

Referring to FIG. 7A, therein is depicted a motor 730 hermetically sealed within a housing 714. A cavity, recess, runner, slot, or other structure 760 may be arranged along an inner surface of housing 714. As depicted in FIG. 7B, motor 730 may include a projection, protrusion, ridge, or other element 762 configured to be positioned within slot 760 to prevent rotation of motor 730 when motor 730 is active rotating a drive element, such as a threaded rod. In some embodiments, slot 760 may be a component affixed or otherwise rigidly arranged along an inner surface of housing 714. In other embodiments, slot 760 may be formed as a cut-out within an inner surface of housing 714. Slot 760 may have various shapes configured to receive a corresponding shape of projection 762. For example, in one embodiment, slot 760 may have a trapezoidal shape configured to receive a corresponding trapezoidal projection 762 of motor 730 (for instance, the same or similar to a dovetail joint). During manufacturing, motor 730 may be positioned within an adjustment device by sliding projection 762 to slot 760, such that motor is held in place by the engagement of projection 762 and slot 760 to prevent axial rotation of motor 730. FIG. 7C depicts a top-down cross sectional view of motor 730 installed within housing 714 with projection 762 arranged within slot 760

Accordingly, in one embodiment, housing 714 may include a slot 760 in the form of a cut-out feature located in an inside surface the hermetic tube of housing that allows motor 730 to translate axially and not rotate about its axis. A blind end 761 of slot 760 may operate to fix the position of motor 730 within housing 714. In some embodiments, an external surface of a motor housing may have a longitudinal projection 762 that locates inside slot 760 with a trapezoidal cross-section (for example, with a dimension of 1 millimeter by 1.4 millimeter by 0.5 millimeters).

Figure 7D:
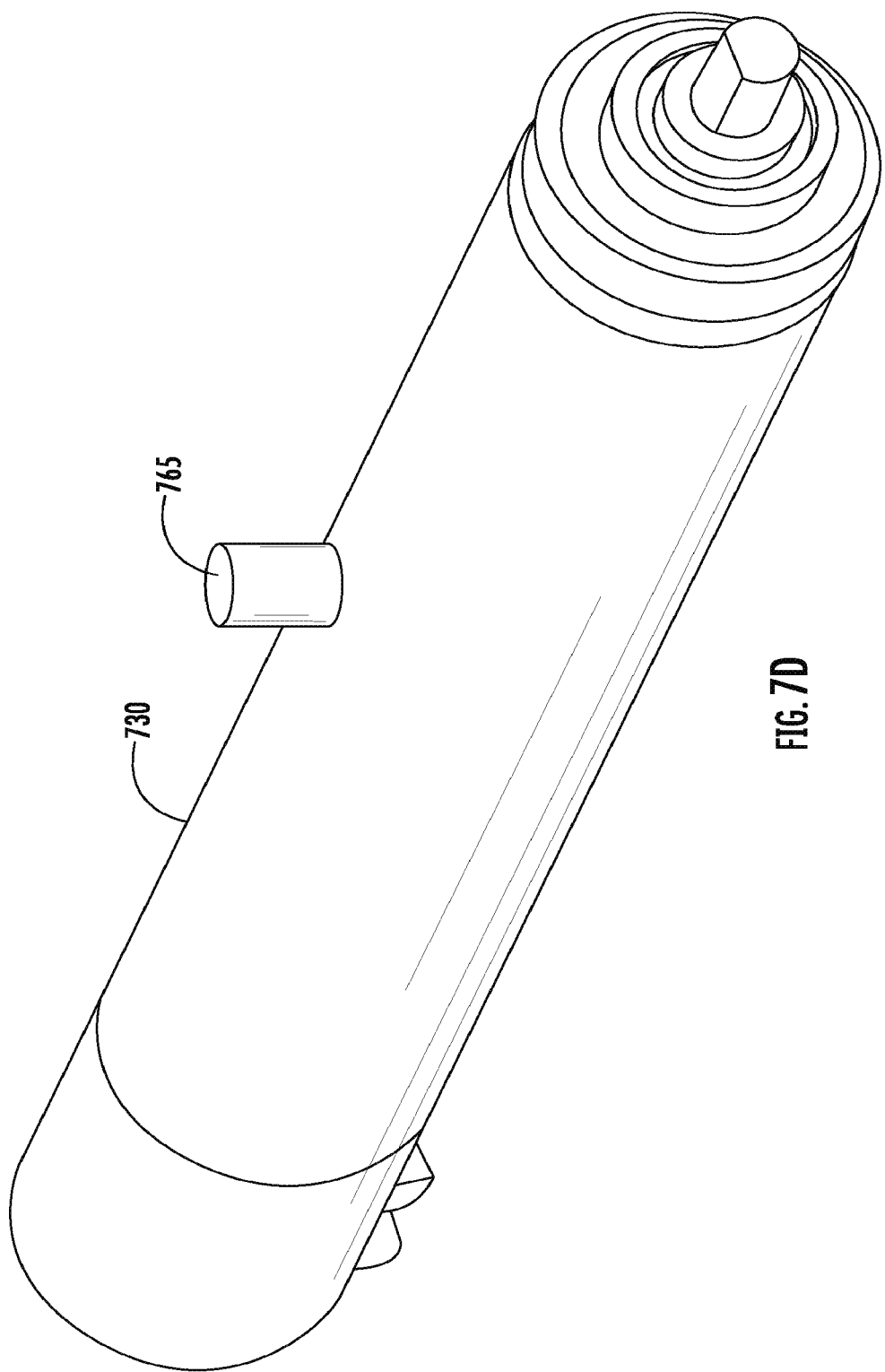

Referring to FIG. 7D, in an alternative embodiment, the outer surface of a housing of motor 730 may include at least one post-like projection 765 configured to engage slot 760 or another corresponding portion of an inner surface of housing 714 to prevent rotation of motor 730. For instance, projection 765 may be formed the same or similar to a dowel pin to engage a corresponding portion of housing 714 to prevent axial rotation of motor 730.

Figure 8A:
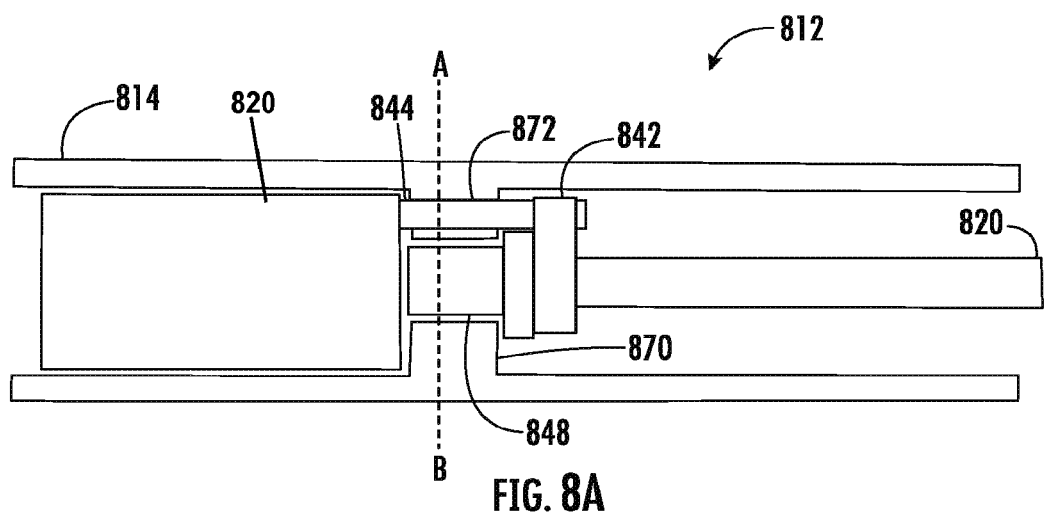
FIGS. 8A and 8B depict a block diagram of an example embodiment of a drive assembly of an implantable bone adjustment device in accordance with one or more features of the present disclosure.
Figure 8B:
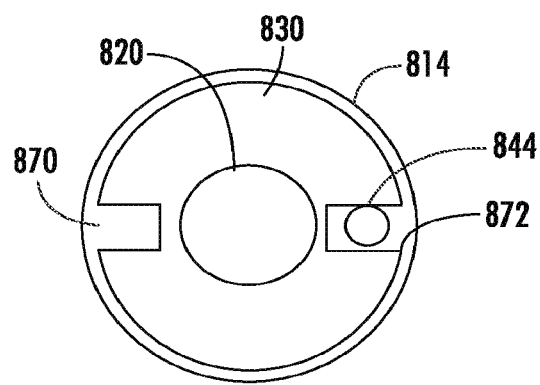

FIGS. 8A and 8B depict a block diagram of an example embodiment of a drive assembly of an implantable bone adjustment device in accordance with one or more features of the present disclosure. Referring to FIG. 8A, therein is depicted a longitudinal section of a drive assembly 812 having a motor 830 hermetically sealed within a housing 814. Motor 830 may be operably coupled to a thrust bearing 848 and a gear 842. A drive element 820, such as a threaded rod, may be operably coupled to motor 830. Actuation of motor 830 may cause gear 842 to rotate axially, thereby causing drive element 820 to rotate. In some embodiments, motor 830 may include a spindle 844. In various embodiments, housing 814 may include one or more steps 870, 872 or similar structures, for example, to facilitate isolation of motor 830 and prevent motor 830 from rotating on its own axis during operation. FIG. 8B depicts an axial cross section through the line A-B of FIG. 8A.

Figure 9A:
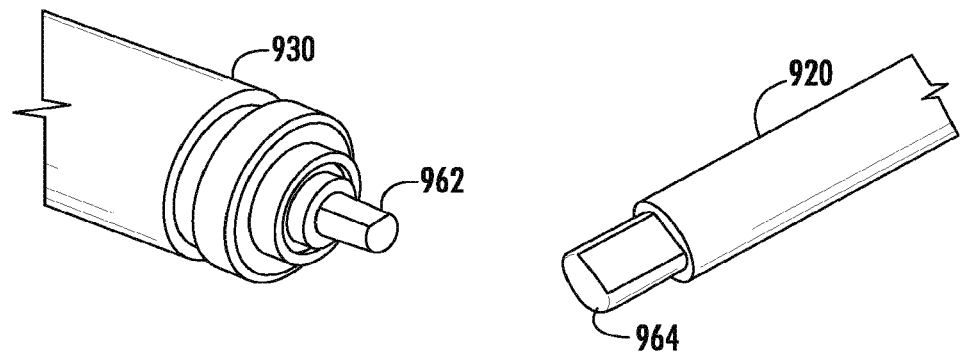
FIGS. 9A and 9B depict an example embodiment of a motor-threaded rod coupling configuration of an implantable bone adjustment device in accordance with one or more features of the present disclosure.
Figure 9B:
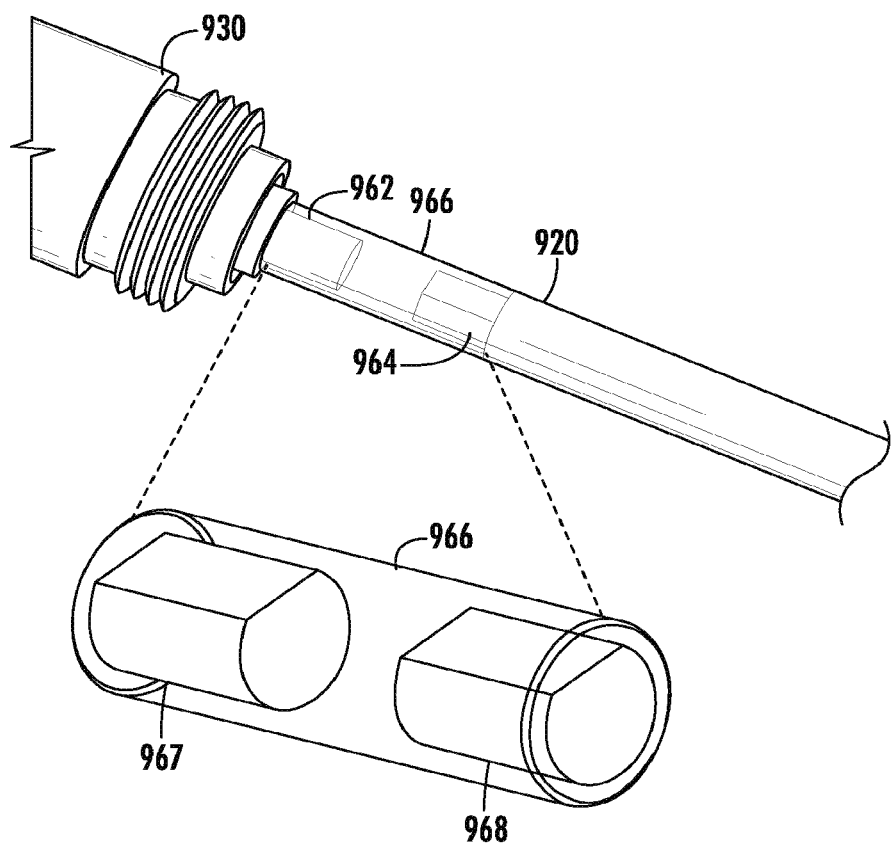

FIGS. 9A and 9B depict an example embodiment of a motor-threaded rod coupling configuration of an implantable bone adjustment device in accordance with one or more features of the present disclosure. In some embodiments, a drive element, such as a threaded rod, may be attached directly to a motor and/or an element rotated by the motor (such as a gear, bearing, and/or the like). In various embodiments, the motor may operate to rotate a spindle or other element that is coupled to a drive element.

As shown in FIG. 9A, a motor 930 may operate to rotate a spindle 962. A drive element 920, such as a threaded screw, may include a lead screw end 964. Spindle 962 may be operably coupled to drive element 920 using a coupling device 966. In some embodiments, coupling device 966 may include a spindle cavity 967 configured to receive an exposed end of spindle 962 and a driving element cavity 968 configured to receive lead screw end 964 of drive element 920. Spindle 962 and/or lead screw end 964 may be rigidly fixed within spindle cavity 967 and/or driving element cavity 968, respectively, using various techniques, such as adhesives, friction fit, compression fit, and/or the like. By connecting spindle 962 to drive element 920 via coupler 966, axial rotation of spindle 962 may cause corresponding axial rotation of coupler 966 and, therefore, drive element 920.

Figure 10:
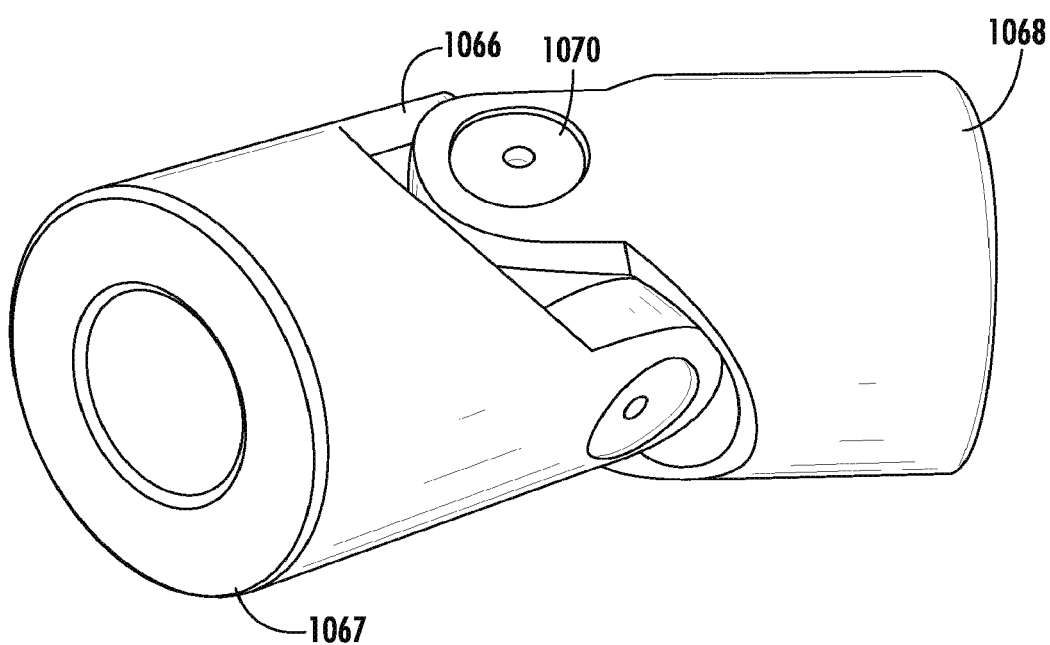
FIG. 10 depicts an example embodiment of a coupler for a motor-threaded rod coupling configuration of an implantable bone adjustment device in accordance with one or more features of the present disclosure.

FIG. 10 depicts an example embodiment of a hinged coupler for a spindle-driving element coupling configuration of an implantable bone adjustment device in accordance with one or more features of the present disclosure.

In some embodiments, a coupling device 1066 may include a spindle cavity 1067 configured to receive an exposed end of a motor spindle (or other element rotated by a motor) (not shown) and a driving element cavity 1068 configured to receive lead screw end of drive element (not shown). In some embodiments, coupler 1066 may have one or more movable or flexible portions, such as a hinge 1070, to facilitate movement of a spindle of a motor and/or a drive element coupled to the spindle via coupler 1066. For example, portions of coupler having spindle cavity 1067 and driving element cavity 1068 may be allowed to at least partially rotate with respect to each other.

Figure 11A:
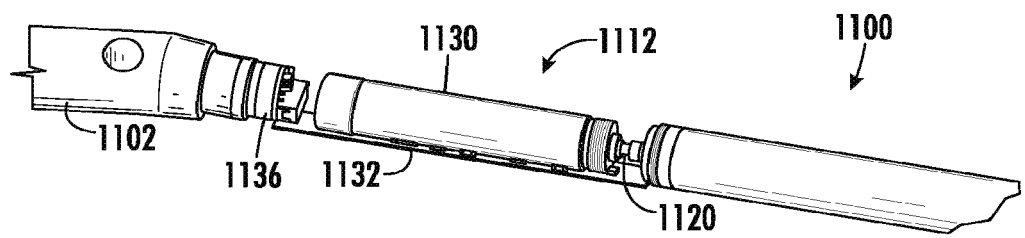
FIGS. 11A-11C depict a third example embodiment of a drive assembly of an implantable bone adjustment device in accordance with one or more features of the present disclosure.
Figure 11B:
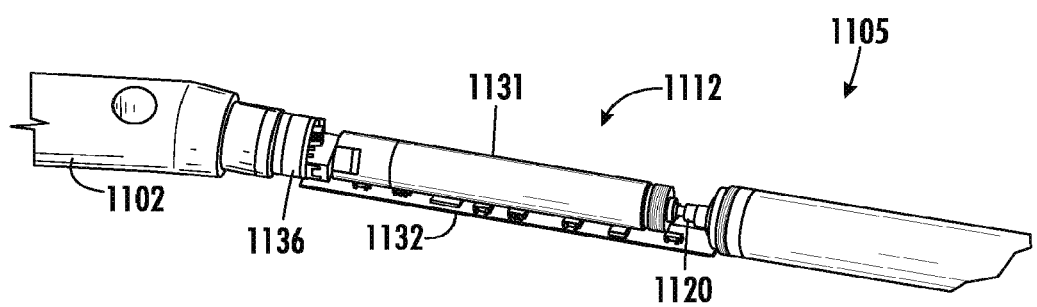
Figure 11C:
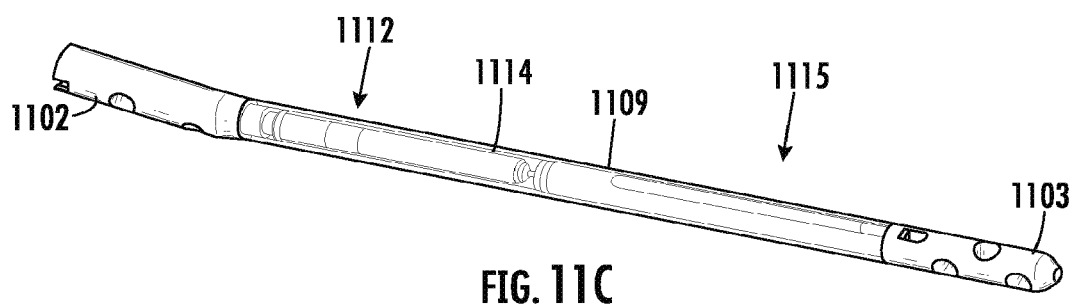

FIGS. 11A-11C depict a third example embodiment of a drive assembly of an implantable bone adjustment device in accordance with one or more features of the present disclosure. In some embodiments, adjustment devices may include LLN of different sizes. For example, drive assemblies according to some embodiments may be configured to fit within 8, 9, and 11 millimeter LLNs using either a 6 millimeter or a 9 millimeter motor. In various embodiments, adjustment devices may include LLNs with a 6 or 8 millimeter diameter motor with integrated gear box (for instance, with an 850:1 gear reduction) and encoder that negates the need for supplementary spur and pinion gears. For example, if the leadscrew supports the thrust forces generated using thrust bearings, then the gearbox may only have to handle the torque. Coupling a driving element, such as a lead screw or threaded rod to the motor shaft may provide flexibility built into the component to handle misalignment and deformations. For example, a small cap welded to the motor and a pin that runs through the screw and into the cap, may be used to allow for some off-axis rotations about the pin.

Referring to FIG. 11A, therein is depicted a portion of an LLN 1100 with an 8 mm diameter motor 1130, distal portion 1102, and drive assembly 1112 having a motor 1130, control system 1132, battery 1136, and drive element 1120. A non-limiting example of motor 1130 may include motor ECXSP08M BL KL A STD 6V, gearhead GPX08 (1296:1), and sensor ENX08 EASY 8IMP, provided by Maxon Motor AG of Sachseln, Switzerland.

Referring to FIG. 11B, therein is depicted a portion of an LLN 1100 with a 6 mm diameter motor 1131. A non-limiting example of motor 1130 may include motor ECXSP06M BL KL A HP 3V, gearhead GPX06 (854:1), and sensor ENX 6 MAG A 8IMP, provided by Maxon Motor AG.

Referring to FIG. 11C, therein is depicted a 9 mm diameter LLN, depicting a proximal end 1102, distal end 1103, and drive assembly 1112 hermetically sealed within housing 1114 arranged within outer housing 1109.

FIG. 12 depicts an example embodiment of control circuitry of an implantable bone adjustment device in accordance with one or more features of the present disclosure. As shown in FIG. 12, a control system or circuitry 1232 may be formed as a circuit board, such as a printed circuit board (PCB) configured to support and/or connect various electrical elements, for instance, surface mounted to control system 1232. Non-limiting examples of electrical elements may include capacitors, inductors, resistors, control units, memories, communication devices, encoders, and/or the like. For example, a master control unit MCU 1272 may be arranged on control system 1232. In another example, a charging circuit 1234 may be arranged on control system 1232. In additional examples, an RF transceiver (or chip), Bluetooth transceiver, NFC transceiver, or other communication interface (not shown) may be arranged on control system 1232.

In a further example, sensors, such as pressure or force sensors, strain gauges, piezoelectric sensors, or other elements for determining operational features of an adjustment device and/or components thereof (for instance, a motor) may be arranged on control system 1232. For example, a (fine) position sensor may include an incremental optical encoder that may operate via pulses/counts directly read by an MCU, status logging directly into non-volatile memory continuously, providing absolute position feedback, and/or other features. In another example, a current sensor may include a sense resistor and differential amplifier operative to, for example, monitor motor current to detect spikes from the motor that may negatively impact on prescription plan. In a further example, a temperature sensor may include, for example, a LMT70 analog temperature sensor located on PCB, a NTC thermistor, or a thermoelectric sensor. An NTC thermistor is configured to, among other things, monitor overheating, overload, insufficient cooling of the motor, and/or other temperature-based issues to protect components of the adjustment device, such as thermal protection of coil windings. In an additional example, a load/torque sensor may be provided on the motor to determine distance travelled by release of energy into motor, energy stored on the capacitor, and/other operational information. The load/torque sensor information associated with DC motor current correlating with torque load on motor may be used, for example, for a tailored distraction rate/frequency, interactive physiotherapy, and/or other personalized treatment options.

Non-limiting examples of system monitoring may include patient compliance/treatment plan, distraction length, lengthening direction, rate and rhythm of distraction, total amount of distraction, lengthening schedule, number of turns of the motor/gear assembly, date and time, battery life/voltage, error events (over current, over voltage, motor temperature), force-feedback during lengthening, and/or the like.

In some embodiments, control system 1232 may include hardware and/or software (for example, firmware) operative to control elements and features of an adjustment system. For example, control system software may receive adjustment information from a computing device (such as computing device 110) and operate components of adjustment system accordingly. For example, MCU or another control element may be configured to execute a prescription (such as implementing an extension distance per time period (for instance, millimeters per day)), operate according to a direct instruction (for instance, an instruction to extend X mm), transmit status or other operational information to a computing device, and/or provide error handling (for example, transmit an error code, message, or other signal response to failure to extend an instructed distance, motor failure, and/or the like).

In various embodiments, the firmware may provide low-level control for the adjustment system (for instance, an LLN) specific hardware. For example, the firmware may operate as a software middleman that allows the PCB hardware to talk to the software (for instance, a Windows® or other computing device operating system). The PCB board (for instance, a flex rigid board) may have enough space to accommodate full-sized programming connectors.

In one specific and non-limiting example, the power needed from the battery to support a full firmware file transfer over Bluetooth, for example, which may roughly consist of 500 data packets, may be approximately 2 mAh with each send requiring about 2 ms. Furthermore, the current needed may be 25 mA over a period of 5 minutes. Therefore, the file transfer may be stretched out over a longer period of time to deliver the necessary energy more slowly. To provide recovery time, the processor may be placed into deep sleep mode given that the normal run current for the processor is >2 mA and for the battery to recover, the current needs to be <100 µA. A consistent and reliable interval between packets from an external computing device (e.g., PC, smartphone) may be implemented to facilitate the device being ready to receive the next packet.

In some embodiments, battery life during firmware updates may be improved using a hub device, for example, which connects BLE to USB and Ethernet. The BLE-Ethernet hub may be used to download firmware files to the adjustment device using a wireless connection, such as a BLE connection using a simple terminal program, and then connect to a board via BLE and execute a file transfer and boot load to that board. The hub device can be used to manage the file transfer to the adjustment device, and given that the BLE in the hub is controlled, the timings can be controlled in such a way that the adjustment device PCB can be set to sleep as necessary during the file transfer process in order to rest their battery.

The configuration of implantable bone adjustment devices may (such as the devices shown in FIGS. 2-12 and/or components thereof) be structurally designed based, at least in part, on load bearing (for instance, axial loads) considerations.

Figure 17:
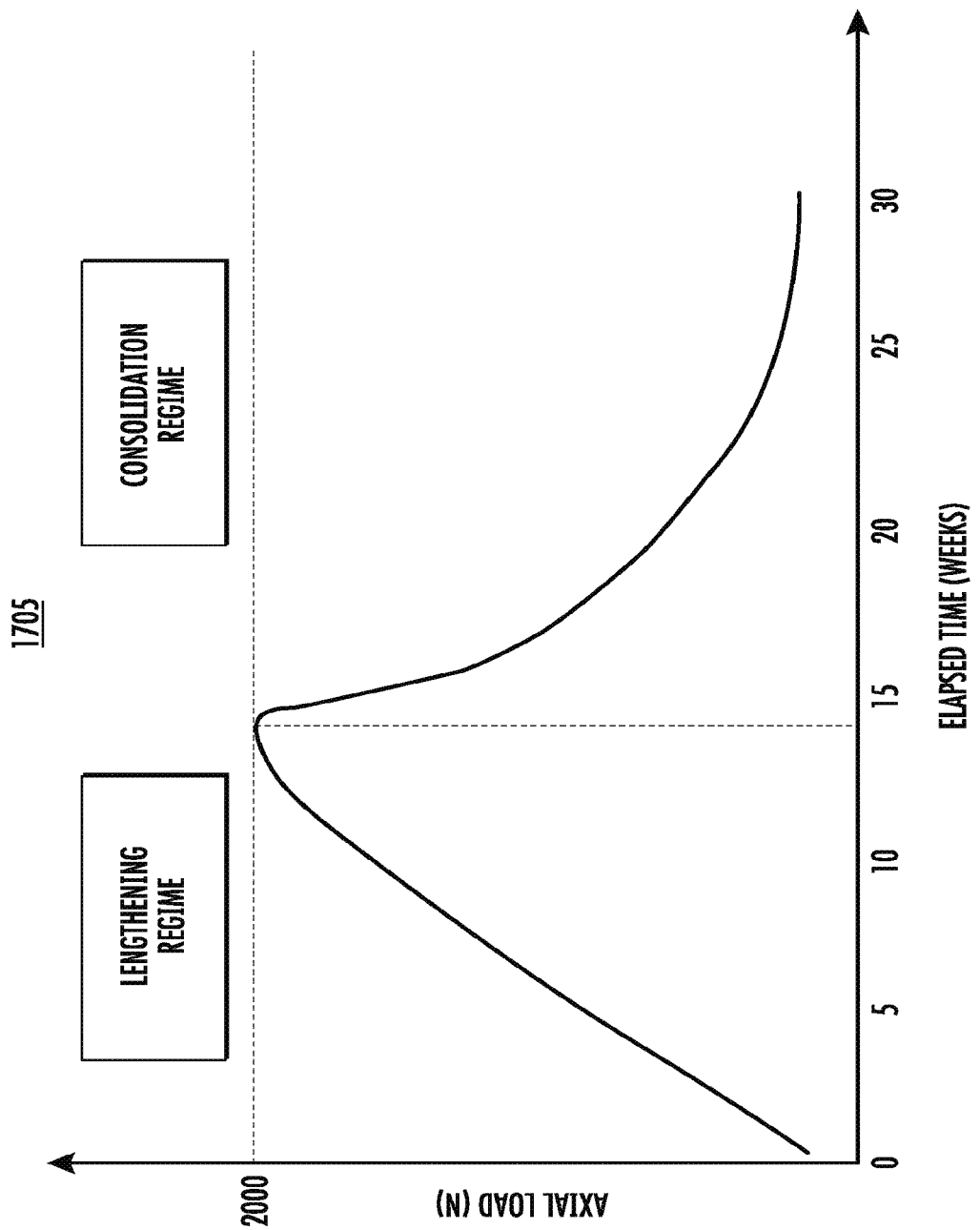
FIG. 17 depicts a graph of axial load versus elapsed time for an implantable bone adjustment device in accordance with one or more features of the present disclosure.

For example, during the lengthening phase, an implantable bone adjustment device may be subjected to axial compression (as well as other forces). FIG. 17 depicts a graph 1705 of axial load versus elapsed time for an implantable bone adjustment device in accordance with one or more features of the present disclosure. As shown in graph 1705, the magnitude of the axial load may increase linearly until the desired length has been achieved. An implantable hone adjustment device may be configured to carry this load through a desired path within the device. However, some of the load may prefer to flow along other (secondary) paths, such as the casing due to manufacturing variations, material homogeneity, and/or other causes. Thus, the most critical components from structural integrity considerations are those in the load path. The load path may be identified by a hypothetical curve drawn between the two ends of an implantable bone adjustment device. For example, the load may be received from the interlocking screws that provide fixation at the bone/implant interface. On the distal side of the implantable bone adjustment device, one screw may pass through the cap of the distraction housing or tube, which may be the location where the load enters the device. The distractor tube may be directly subjected to the load; accordingly, it may reside on the load path. The load may then be transmitted from the distractor tube to the lead screw though its threading. Further downstream along the load path, the load may be transmitted though the flange of the lead screw to the frame of the drive system, for example, via a combination of miniature bearings and a support ring. The risk of damaging the driveshaft/gearhead is mitigated by transmitting the load, at least in part, directly to the drive system housing/frame. Accordingly, the structural design of implantable bone adjustment devices according to some embodiments may include a desired load transfer path so that components that reside along this route, (e.g., lead-screw and distractor tube) may be distinguished from those that do not, by applying a different factor of safety.

Changes in tensile force in quasi-continuous and step lengthening methods may occur throughout the lengthening process (see, for example, Ohnishi et al, "Measurement of the Tensile Forces During Bone Lengthening," Clinical Biomechanics, 20(4), pp. 421-427 (2005). For example, during the initial stage of lengthening, the tensile forces may increase almost linearly with the increase in hone length. However, no significant change in the average increment of the load per unit length gain between quasi-continuous and step lengthening may occur.

FIGS. 13A-13D depict example embodiments power systems for an implantable bone adjustment device in accordance with one or more features of the present disclosure.

Figure 13A:
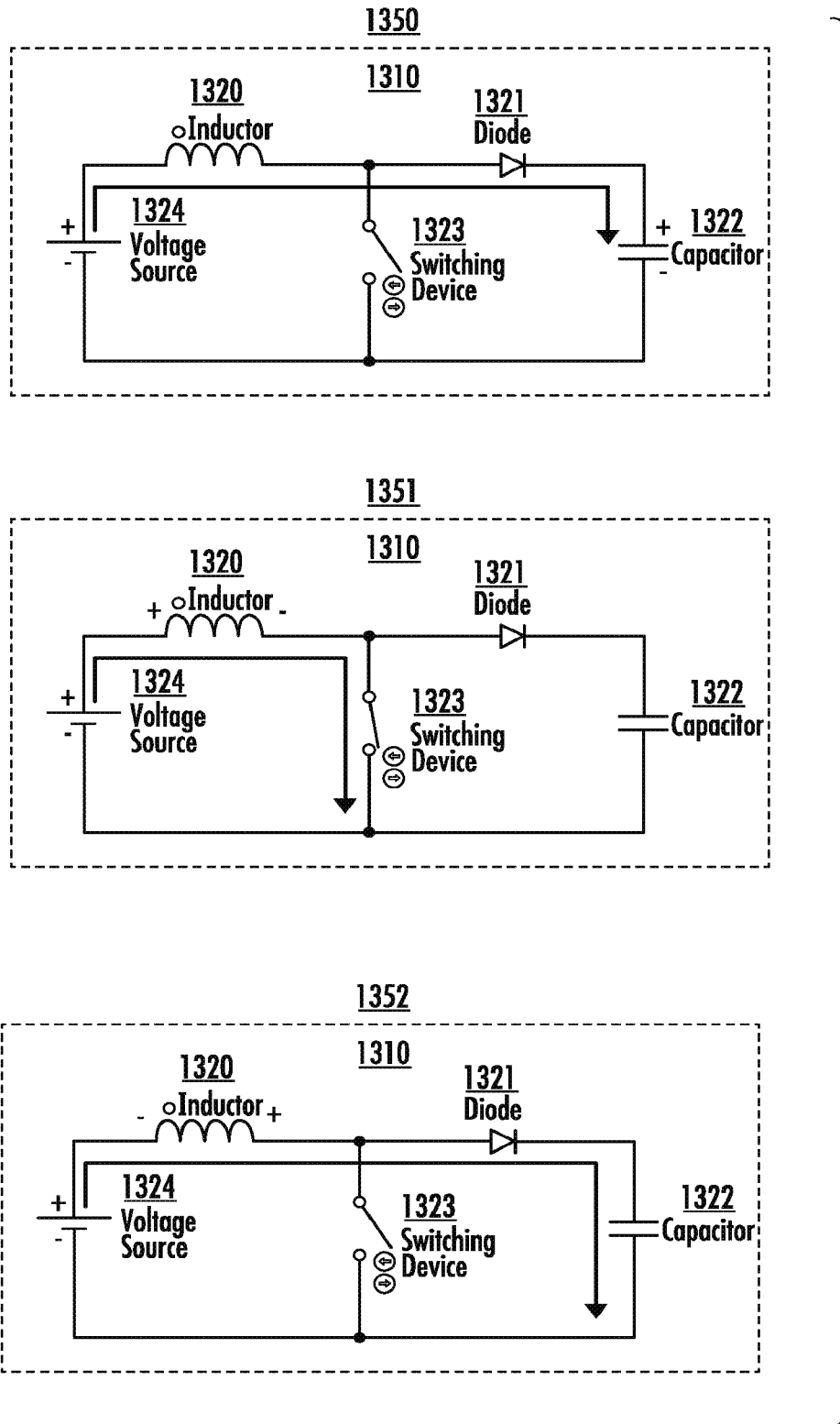
FIGS. 13A-13D depict example embodiment of power systems for an implantable bone adjustment device in accordance with one or more features of the present disclosure.

Referring to FIG. 13A, therein is depicted an example embodiment of a power management system for a drive assembly of an implantable bone adjustment device in accordance with one or more features of the present disclosure. More specifically, FIG. 13 depicts various states of a power management system (or "charge pump") that may be used to manage power features of an adjustment system in accordance with the present disclosure. A charge pump 1310 may include an inductor 1320, a diode 1321, a capacitor 1322, a switching device 1323, and/or a voltage source 1324 (for instance, a battery). Each adjustment device (for instance, an LLN) may be equipped with a charge pump circuit as part of the overall power management system. In some embodiments, the motor is driven in short increments from the charged capacitor allowing for conservation of "stored energy" for powering the struts (driver or lead screw) at any given time. When the voltage on the capacitor reaches a threshold level (for instance, about 20V), the stored energy is released as a "pulse" into the geared motor. The pulses can also be released in two directions: forward and reverse. In some embodiments, one full rotation of the motor may require about 20 discharges. In various embodiments, the capacitor is charged once per minute to the target voltage over a 1-4 s period.

State or step 1350 may include a "switch-off" step in which $O_C$ is charged to $I_V$ (3 volts); a one diode drop. Step 1351 may include a "switch-on" step in which current is diverted through MOSFET. Step 1352 may include a "switch-off" step in which $O_C$ is charged to 20 volts (change in polarity of I).

For example, a power cell may cause a motor to turn, thereby rotating a threaded rod. "Stored energy" may be conserved for powering the motor at any given time. There may be a build-up, for example, of 20 volts (or other required voltage), on the capacitor so it is released as a "pulse" into motor, which can be released as a pulse in two directions. In some embodiments, one full rotation of the motor may require a certain number of discharges, for example, about 20 discharges. The capacitor may be charged once per minute to target voltage over 1-4 s. In addition, voltage may be stepped down to protect other electrical components (for instance, a Bluetooth chip, encoder, and motor)

In another example, the capacitor may be charged first, for example, from a battery whose voltage is lower than the voltage on the charged capacitor. For instance, the circuit can be charged in 400 milliseconds at a pulse rate of 100 kilohertz. Circuit typically charges a capacitor to a certain voltage, such as 20 volts, and then discharges into the motor. In one embodiment, the power circuitry may measure exactly how much energy was delivered in any pulse and released to motor ($E=0.5*CV2$) via capacitor voltage up to 20 volts. Energy released into the motor windings from this voltage is extremely low, for example, such that damage to winding coils or other components is unlikely. Embodiments are not limited in this context.

A typical implantable bone adjustment device may not require a large amount of power to function. The amount of power needed may depend on the device's functions and voltage specifications, which may be as little as 2-3 volts. Therefore, devices according to some embodiments may be configured to, among other things, minimize the power consumption within the device circuit components and, in some embodiments, to additionally increase device efficiency of power generation, for instance, in an effort to increase the lifespan of the device. For example, in some embodiments, an implantable energy harvester (IEH) interface may be or may be used to supplement the primary power source, for instance, for a rapid top-up of charge of a device power reservoir.

Figure 13B:
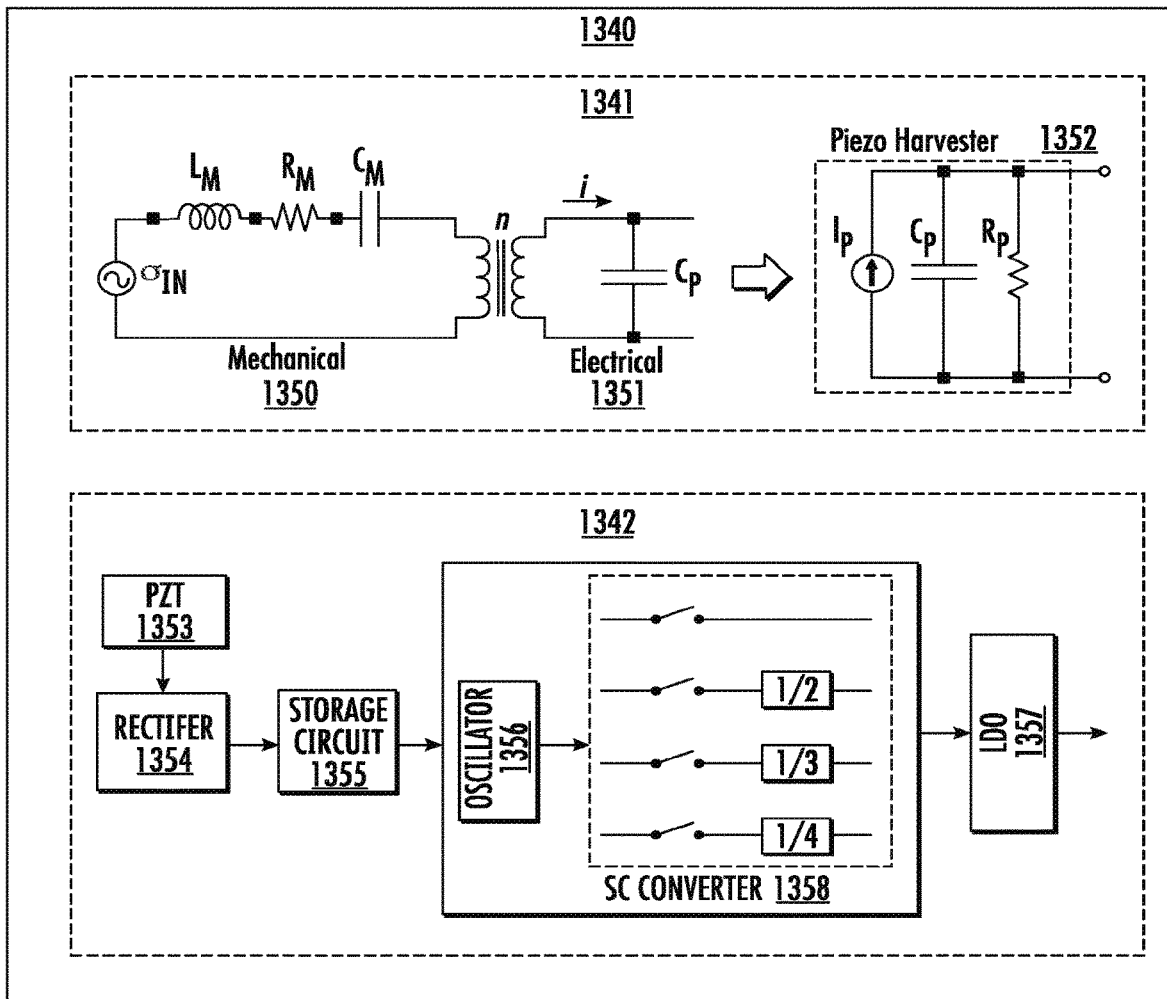
Figure 13C:
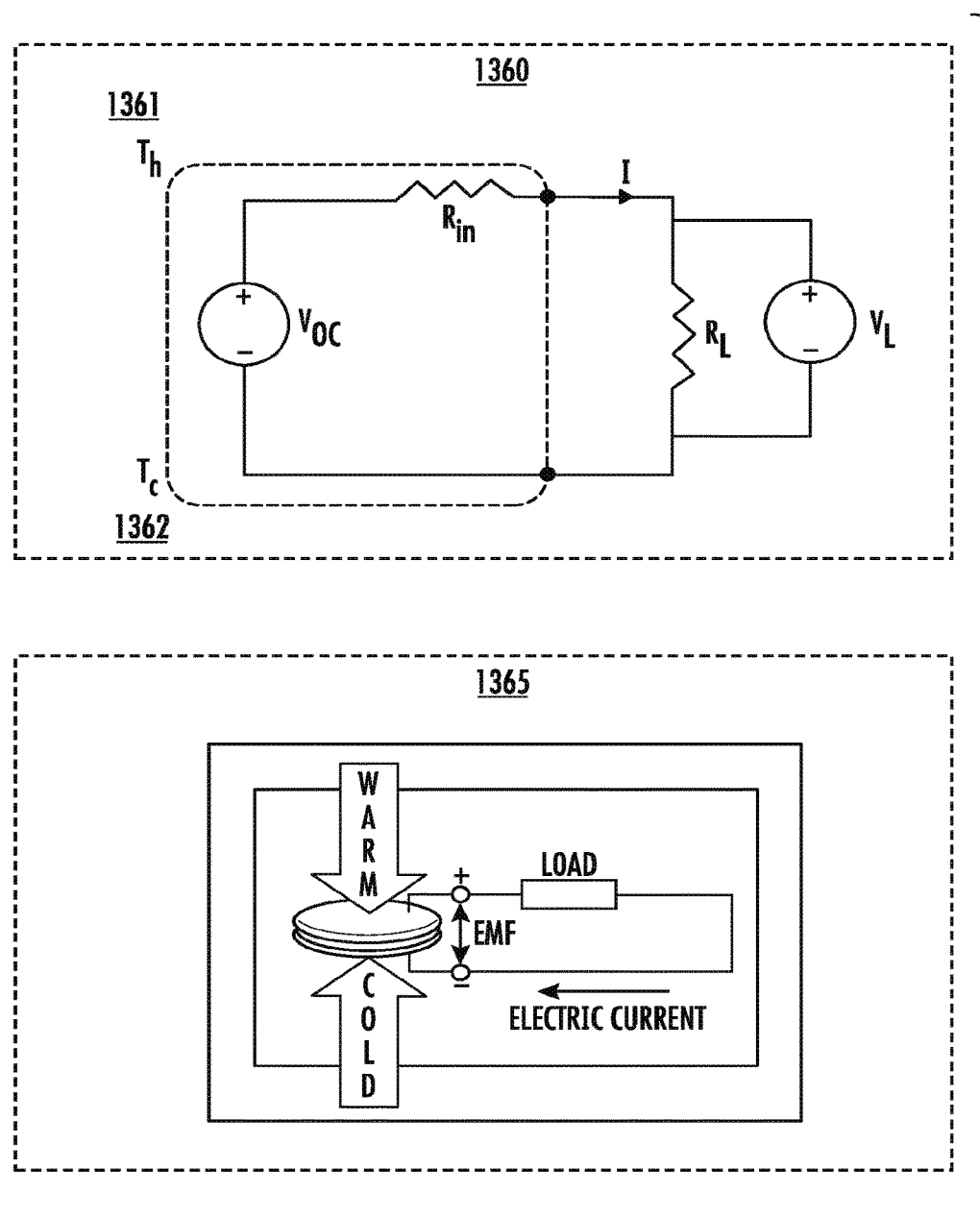
Figure 13D:
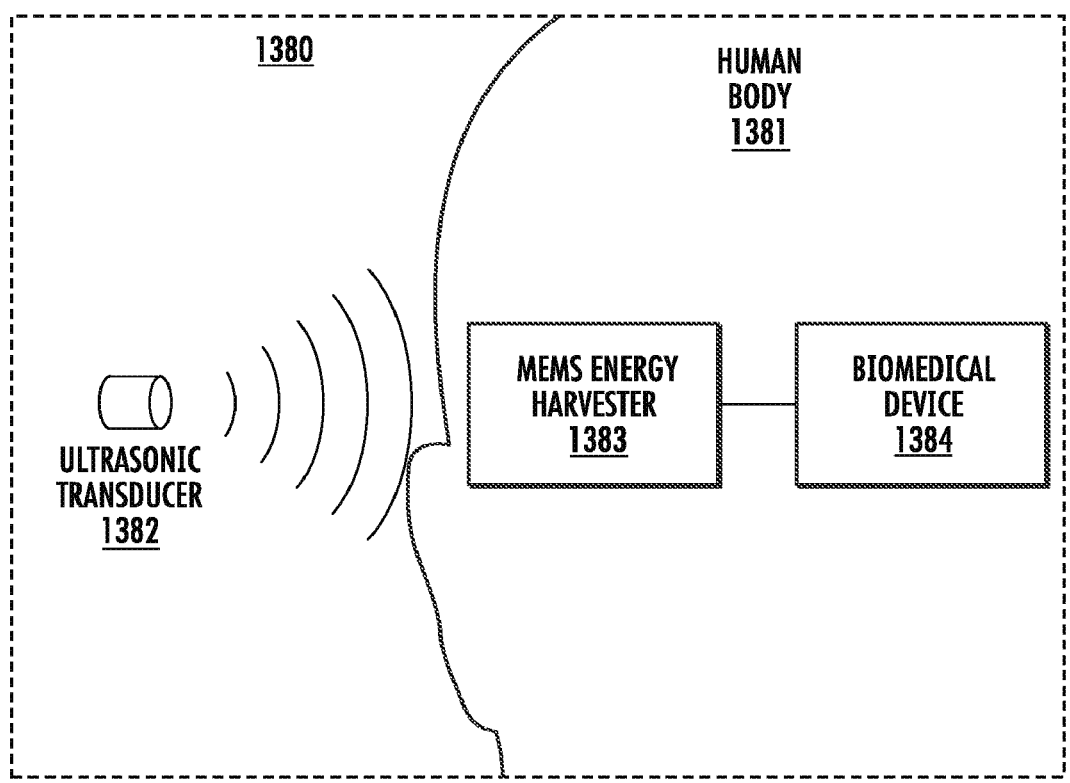

In various embodiments, human energy harvesting sourced from kinetic and thermal energy, for example, using piezoelectric (PEG or PZT) and/or thermoelectric (TEG) generators, respectively, may be used (see, for example, FIGS. 13B-13D). In some embodiments, energy harvesting devices may be configured to generate additional power of, for instance, up to 1 Watt (W). For example, sleeping can produce approximately 81 mW of power, whereas sprinting can produce 1630 mW of power. The human body can also retain (or maintain its) temperature even when the ambient temperature changes. Human energy harvesting can also be supplemented with wireless energy harvesting. A non-limiting example of wireless energy harvesting may include ultrasonic transmission, which converts the energy of surface-applied ultrasound beam to a high-frequency current (for instance, up to 20 nW).

Referring to FIG. 13B, therein is depicted a mechanical (or kinetic) energy harvesting system 1340, that may be used as a power source for an implantable bone adjustment device according to some embodiments. In some embodiments, system 1340 may be or may include an integrated power management circuit for a piezoelectricity converter that includes an electrical circuit for a piezoelectric circuit (for example, PZT) 1341 and a power converter circuit for a piezoelectric generator (for example, a PZT generator) 1342.

In some embodiments, the piezoelectric effect may be used to convert mechanical motion to electrical energy. For an implantable bone adjustment device, mechanical motion may be or may include leg movements of the patient, for example, of the leg in which the implantable bone adjustment device is installed. An electrical circuit 1351 may generate electrical signals from mechanical movements received at a mechanical circuit 1350 that may be harvested by a piezo harvester 1352.

In various embodiments, a rectifier 1354 may be coupled to a piezoelectric harvester (for example, a PZT generator) 1353. Rectifier 1354 may be used to convert alternative current (AC) power into direct current (DC) power. At least a portion of the power from rectifier may be provided to an oscillator 1356, for instance, via a storage circuit 1355. As shown in FIG. 13B, power management system 1340 may include serial connections of a variable step-down ratio switched-capacitor (SC) DC-DC converter 1358 and a low dropout linear regulator (LDO) circuit 1357. In various embodiments, a function of variable step-down ratio SC 1358 and LDO circuit 1357 is to regulate the output voltage of storage capacitor and the input voltage, respectively.

Referring to FIG. 13C, therein is depicted a thermoelectric generator (or TEG) 1360. In general, a thermoelectric generator contains a large number of thermocouples connected electrically in series with high thermal resistance and thermally in parallel to form a thermopile. A thermo-electric harvester can produce minimal power from the temperature difference: $T_h$ (1361)=hot and $T_c$ (1362)=cold (e.g., via the Seebeck effect).

As shown in 1365, thermoelectric generator 1360 may operate to generate power (for instance, an electromotive force (EMF)) due to a temperature difference between two dissimilar electrical conductors (or semiconductors) that produces a voltage difference between the two substances. In some embodiments, the "warm" temperature may be due to patient body temperature and the "cold" temperature may be due to ambient air temperature (or the effect of ambient air temperature on a portion of the body of the patient). In other embodiments, the "warm" and "cold" temperatures may be due to temperature gradients between different internal portions of the body. The terms "warm" and "cold" may be relative and not related to absolute temperatures. For example, the temperature difference between "warm" and "cold" be 1° C. or less. Embodiments are not limited in this context.

Referring to FIG. 13D, therein is depicted an ultrasonic energy transmission system 1380 according to some embodiments. System 1380 may include an ultrasonic transducer 1382 and an energy harvester (e.g., a Micro-electro-mechanical systems (MEMS) energy harvester 1382) configured to receive ultrasound waves from ultrasonic transducer 1382. Energy harvester 1382 may operate to convert the energy of a surface-applied ultrasound beam from ultrasonic transducer 1382 to a high-frequency current that may be used by a biomedical device 1384 operably coupled to energy harvester 1383. In various embodiments, biomedical device 1384 may be an implantable bone adjustment device, such as an LLN. Ultrasonic transducer 1382 may be a generator fixed onto or brought near to the skin and coupled to energy with a biosensor. The energy harvester 1382 may be arranged inside a body 1381 to absorb the ultrasound energy and convert it into electrical charge for biomedical device 1384.

Figure 14:
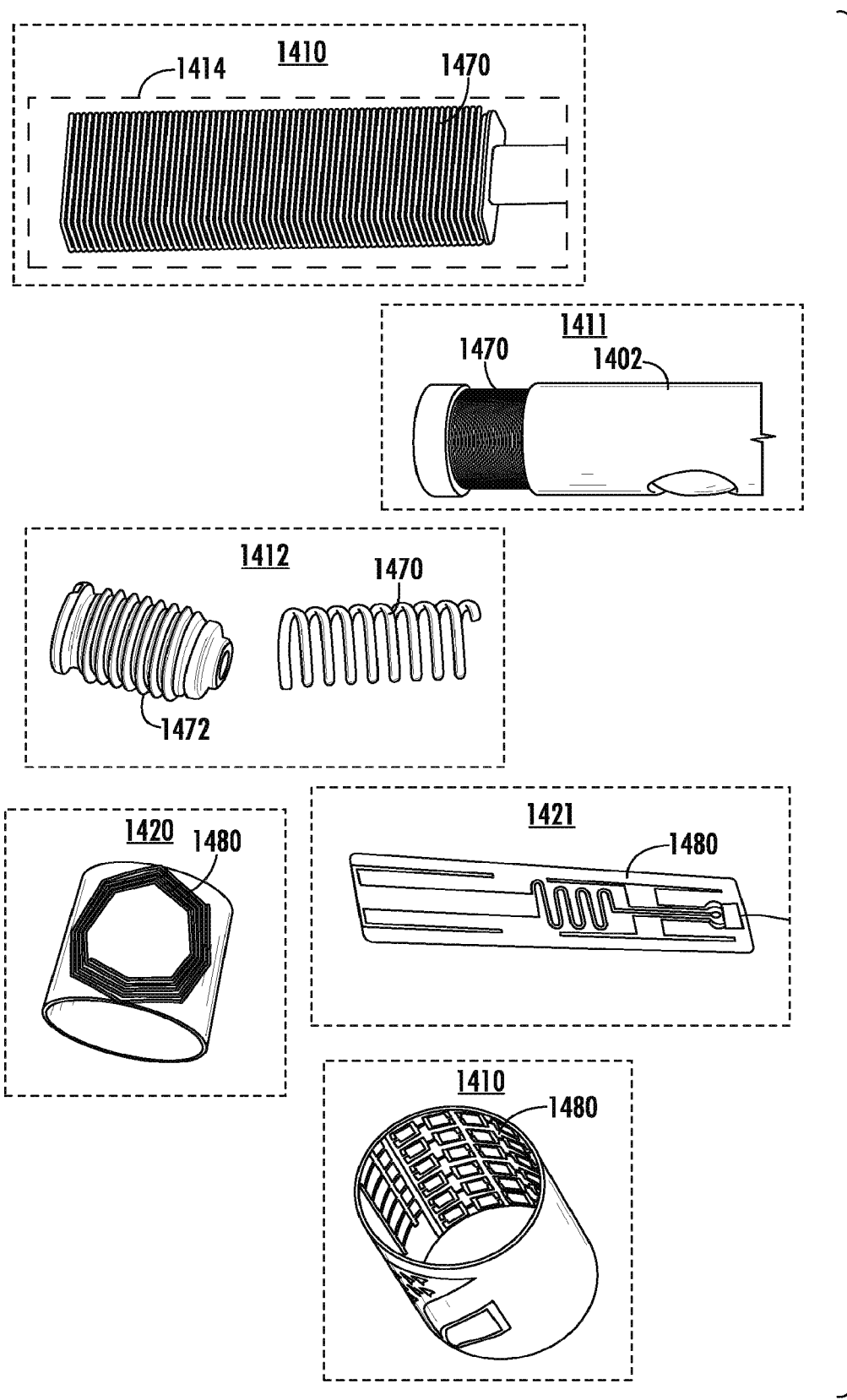
FIG. 14 depicts example embodiments of antenna configurations for wireless communication for a drive assembly of an implantable bone adjustment device in accordance with one or more features of the present disclosure.

FIG. 14 depicts example embodiments of antenna configurations for wireless communication for a drive assembly of an implantable bone adjustment device in accordance with one or more features of the present disclosure. In some embodiments, communication to/from an adjustment system may be implemented via one or more antennas and associated circuitry, chips, and/or the like. In various embodiments, the shape of the adjustment device and the intended implantation site may determine the types of antennas that may be used.

In exemplary embodiments, a helix/coil antenna may be used as depicted in configurations 1410-1412. In 1410, an antenna 1470 may be circumferentially around a block of material (for example, ferrite) located inside the tubular housing (for instance, housing 214, 314, and/or 414). In 1411, an antenna 1470 may be wrapped circumferentially around an end of an LLN 1402. In 1412, an antenna 1470 may be wrapped circumferentially around an end of a nail cap 1472.

In other embodiments, such as depicted in configurations 1420-1422, printed antennas 1480 may be used. Printed antennas may be used, for example, for frequencies 13.56 megahertz, 915 megahertz, and/or 2.4 gigahertz. In 1420, antenna 1480 is printed onto a curved, 3D flexible PET surfaces that can be mounted onto the inside surface of the nail. In other embodiments, inkjet printing technology may be used in the manufacture of conformal structures. In some embodiments, multiple separate antennas may be used for different purposes, such as for wireless data communication, data telemetry (402 megahertz), and a wake-up controller (2.45 gigahertz). Embodiments are not limited in this context.

In another embodiment, a chip antenna may be used. For example, an optional megahertz ISM band element may be used to improve radio signal out of the adjustment device, which is contained in a shielded material. Lower frequency radio signals travel father, and can penetrate better than higher frequency radio signals. Antennas, such as those depicted in FIG. 14, may be mounted, installed, embedded, and/or otherwise affixed in or on various portions of an implantable bone adjustment device, such as an LLN. For example, an antenna may be affixed in or on a cap of an LLN.

Figure 15A:
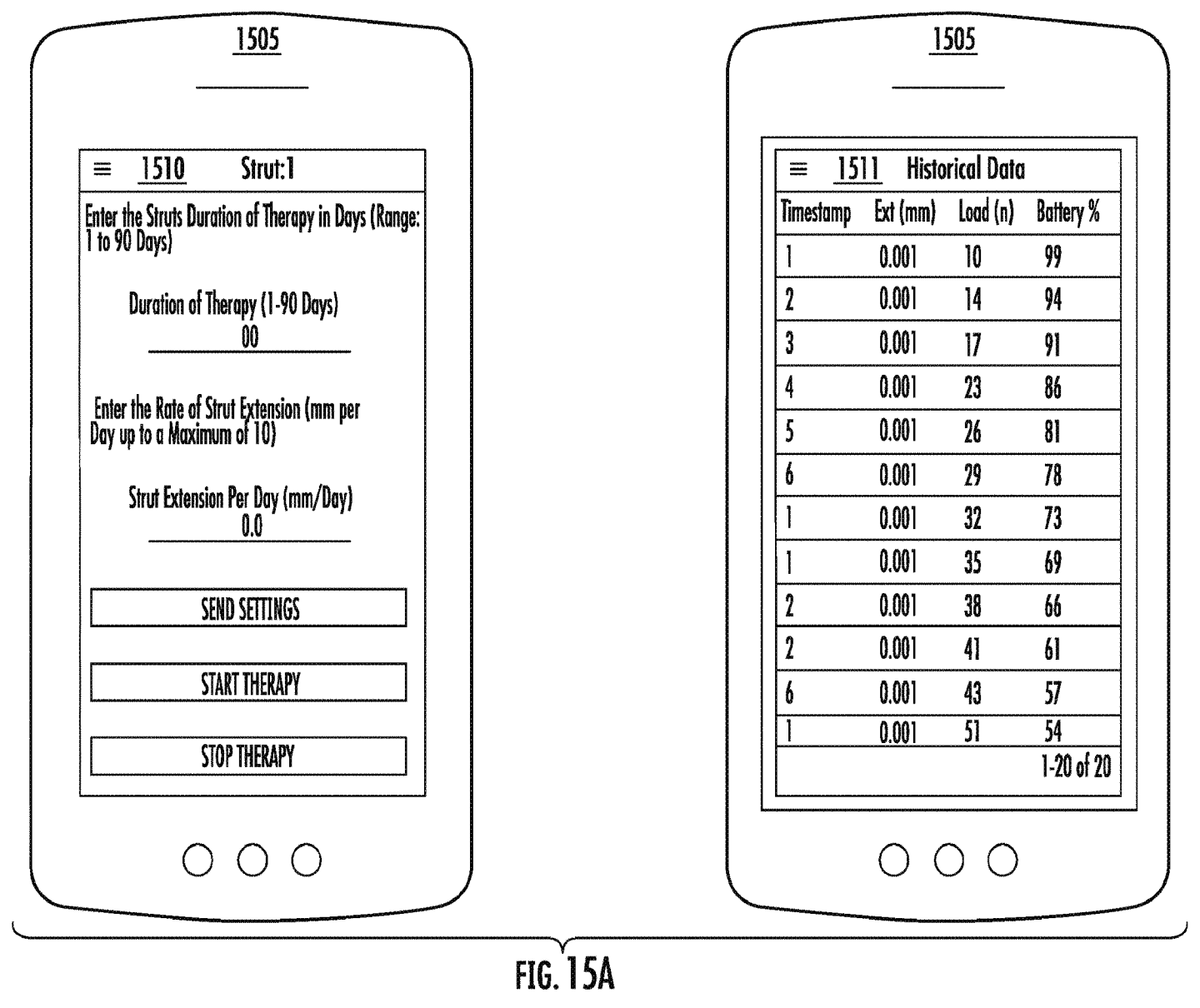
Figure 15B:
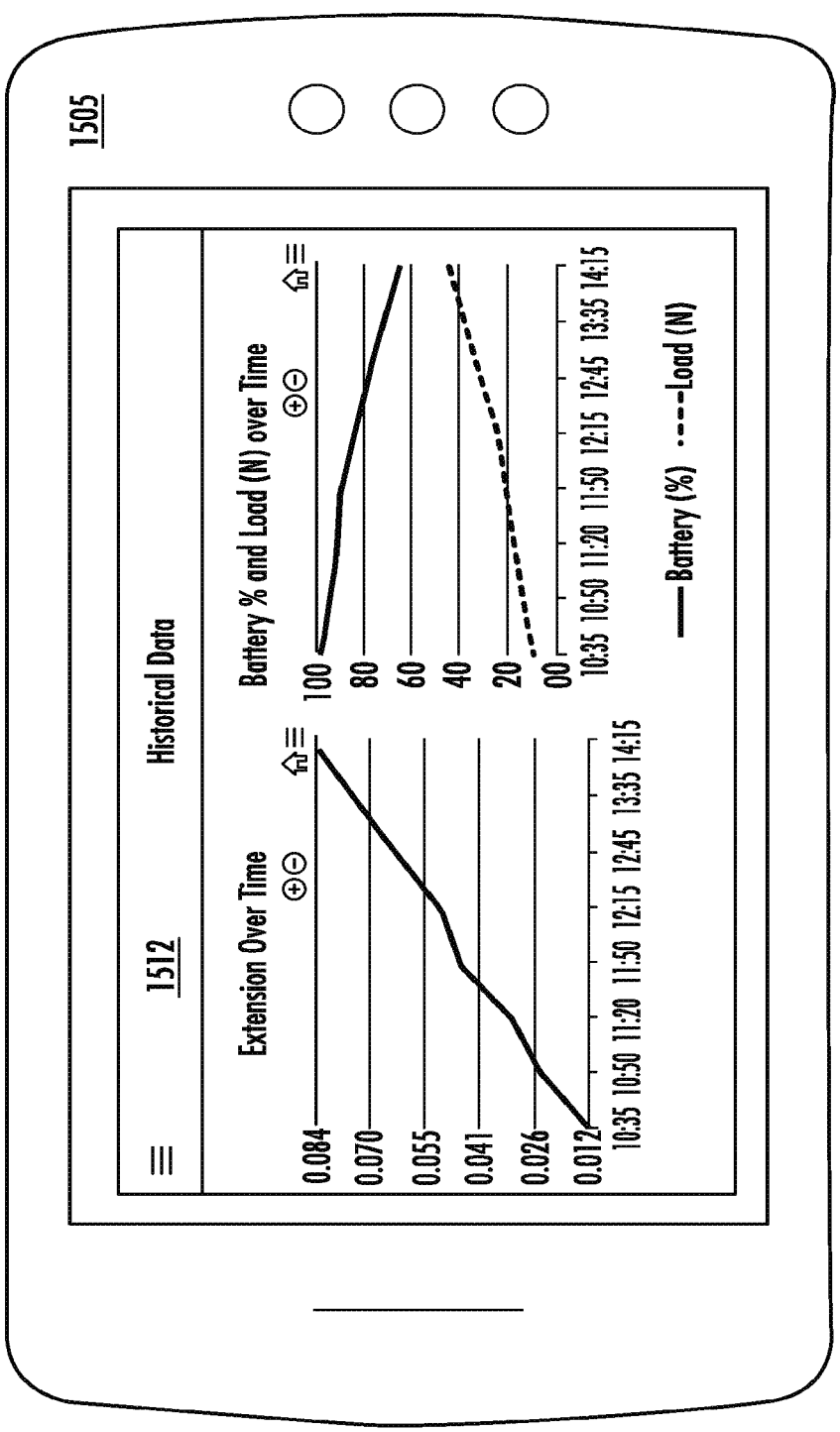

FIGS. 15A and 15B depict example embodiments of graphical user interfaces (GUIs) for a bone adjustment application (companion application or companion "app") for controlling functions of an implantable bone adjustment device in accordance with one or more features of the present disclosure. As depicted in FIGS. 15A and 15B, various graphical user interface (GUI) screens 1510-1512 may be presented via a display of a computing device 1505. For example, GUI screens 1510-1512 may be presented via an application (a "mobile app" or "app") executing on computing device 1505 (for instance, which may be the same or similar to computing device 110). A patient, caregiver, and/or healthcare professional may be able to operate an adjustment device and/or view historical information associated with an adjustment device.

For example, a user may use GUI screens 1510-1512 to upload a prescription to control circuitry of an adjustment system. As shown in FIG. 15A, screen 1510 may allow a user to specify adjustment parameters, such as the duration of therapy, extension distance per day, and/or the like. The parameter information may be received by the control circuitry which, in response, may control a motor to cause an extension of a portion of the adjustment device according to the parameters (for instance, to achieve an extension distance over a specified time period). In some embodiments, an adjustment system, in combination with an adjustment application, may allow for semi-continuous actuation and can monitor the lengthening process to an accuracy of 70 microns assuming adjustments every minute (1440 per day).

Screen 1510 may present historical information, such as a time stamp, an extension distance (for example, a total extension distance, an extension over a specific time period, and/or the like), a force or load, battery percentage, and/or other operating information. As shown in FIG. 15B, historical data may be presented via screen 1512 in a graphical form.

Accordingly, a user may operate and/or view status information of an adjustment device configured according to some embodiments using a computing device, such as a smartphone.

In some embodiments, an adjustment device may be or may include a telescoping IM nail that is actuated by an embedded, hermetically sealed geared electric motor. In some embodiments, motor, optical encoder, communications, and processing functions may be powered by at least one coin cell battery and charging circuit. In some embodiments, communications between a computing device and the adjustment device may be via an RF antenna printed onto the nail body. In some embodiments, the lead screw may have dimensions of about 80 mm long, about 2 mm outer dimension, and about a 0.2 mm pitch threaded rod to draw telescope apart. In some embodiments, the IM nail may extend or retract about 5 cm. In various embodiments, certain moving components may be coated with a lubricous coating, such as diamond-like carbon (DLC) or mineral oil to reduce friction.

In various embodiments, a drive assembly may include a "floating design" motor drive unit displaceable in the axial direction. In some embodiments, a motor may be or may include a fully integrated 12V geared motor (for example, 342:1 ratio), gear reduction (8 millimeter outer diameter×25 mm) with an (optical) encoder. In exemplary embodiments, the motor may be attached or otherwise engaged to and inside surface of the hermetically sealed housing to prevent it from spinning. Constraining the motor minimizes the axial load applied to this component. The threaded rod may be under compression, and reactive forces may be in torsion. In some embodiments, the motor may turn in one of two directions.

Figure 16:
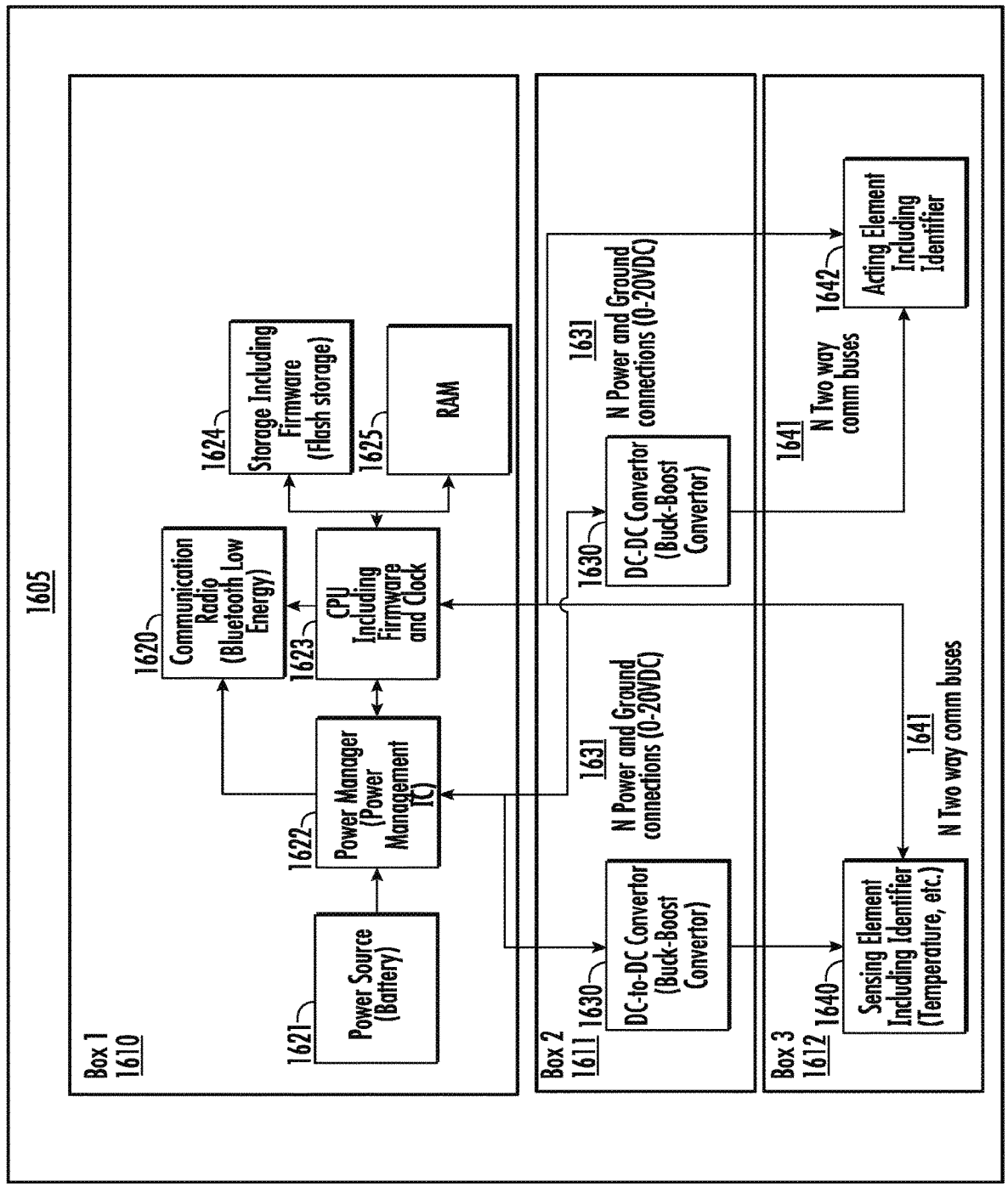
FIG. 16 depicts an example embodiment of a hardware architecture of a control system for a bone adjustment device in accordance with one or more features of the present disclosure.

FIG. 16 depicts an example embodiment of a hardware architecture of a control system for a bone adjustment device in accordance with one or more features of the present disclosure. As shown in FIG. 16, a control system 1605 may include a set of component systems or packages 610-612 that may include electrical and computing components for performing sensing, control, and power operations for a bone adjustment device. A bone adjustment device may include an implantable bone adjustment device according to some embodiments. However, embodiments are not so limited, as control system 1605 may be used to control operational features of other types of hone adjustment devices, such as a Taylor spatial frame (TSF), and orthopedic devices.

In some embodiments, component packages 610-612 may include a control package 610, a convertor package 611, and a device package 612 operably coupled to each other through the depicted bus system to form the main control system 605. The control package 610 may include a communication radio (for instance, a BLE transceiver) 1620, a power source (for instance, a battery) 1621, a power manager (for instance, a power management integrated circuit (IC)) 1622, a CPU (for instance, that may include control firmware and a clock) 1623, storage (for instance, flash storage and/or the like that may store firmware), and memory (for instance, RAM and/or the like) 1625. Converter package 1611 may include one or more DC-to-DC convertors (for instance, a buck boost converter) 1630 and power and ground connections (for instance, 0-20 VDC) 1631. Device package 1612 may include one or more sensors or encoders 1640 and acting elements 1642. In some embodiments, a sensor or encoder 1640 may be or may include various sensors, including an identifier (for instance, temperature, pressure, and/or the like). In various embodiments, sensor or encoder 1640 may include an encoder, such as an optical encoder or IR sensor according to some embodiments. In exemplary embodiments, acting element 1642 may include an element such as a motor configured to perform an action instructed by control components 1610. Device package 1612 may include various buses (for instance, two-way communication buses) 1641 or other circuitry for providing communication among control system 1605 and devices thereof.

In some embodiments, an implantable bone adjustment device (for instance, an LLN) may include control package 1610, for example, within the hermetically sealed housing. In various embodiments, control package 1610 may operate under low power, such as about 3 V to about 5 V. For a TSF or similar strut-based adjustment device, one or more of the struts may include control package 1610 arranged, at least partially, internal to a volume of the strut.

In various embodiments, an implantable bone adjustment device (or a strut of a TSF) may include converter package 1611 for converting voltages as necessary for elements of device package 1612. For example, a hone adjustment device (or a strut of a TSF) may include multiple sensing or encoding elements 1640 (for instance, a rotary encoder and a true position indicator, such as a capacitance sensor strip, IR sensor, and/or the like), with each requiring a different powering voltage. For example, an encoder may require 6 V and the capacitance sensors may require on 12 V. In another example, acting element 1642 (such as a step motor) may be housed in the bone adjustment device (or strut) and may also have different power requirements. Accordingly, for example, DC-DC convertor(s) 1630 may be used to step up the voltage up (for instance, 12 V) in order to power the motor or capacitance sensors appropriately.

Although component packages 1610-1612 are depicted in FIG. 16, a control system 1605 may include less or additional control packages. For example, converter package 1611 may not be included if voltage conversion is not required. In addition, each of component packages 1610-1612 may include less or additional elements. Furthermore, elements of packages 1610-1612 may be included in other of packages 1610-1612. Embodiments are not limited in this context.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

Directional terms such as top, bottom, superior, inferior, medial, lateral, anterior, posterior, proximal, distal, upper, lower, upward, downward, left, right, longitudinal, front, back, above, below, vertical, horizontal, radial, axial, clockwise, and counterclockwise) and the like may have been used herein. Such directional references are only used for identification purposes to aid the reader's understanding of the present disclosure. For example, the term "distal" may refer to the end farthest away from the medical professional/operator when introducing a device into a patient, while the term "proximal" may refer to the end closest to the medical professional when introducing a device into a patient. Such directional references do not necessarily create limitations, particularly as to the position, orientation, or use of this disclosure. As such, directional references should not be limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments. Rather these embodiments should be considered as illustrative and not restrictive in character. All changes and modifications that come within the spirit of the invention are to be considered within the scope of the disclosure. The present disclosure should be given the full scope defined by the language of the following claims, and equivalents thereof. Unless otherwise defined, all technical terms used herein have the same meaning as commonly understood by one of ordinary skill in the art to which the disclosure belongs.

The foregoing description has broad application. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However, such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. Furthermore, references to "one embodiment" of the present disclosure are not intended to be interpreted as excluding the existence of additional embodiments that also incorporate the recited features.

In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with another embodiment to yield a still further embodiment. Thus, it is intended that the present subject matter covers such modifications and variations as come within the scope of the appended claims and their equivalents.

As used herein, an element or step recited in the singular and proceeded with the word "a" or "an" should be understood as not excluding plural elements or steps, unless such exclusion is explicitly recited. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

The phrases "at least one", "one or more", and "and/or", as used herein, are open-ended expressions that are both conjunctive and disjunctive in operation. The terms "a" (or "an"), "one or more" and "at least one" can be used interchangeably herein.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The drawings are for purposes of illustration only and the dimensions, positions, order and relative to sizes reflected in the drawings attached hereto may vary.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

What is claimed is:

1. A limb lengthening nail configured to be implanted within the intramedullary canal of a bone of a patient, the limb lengthening nail comprising:
- a proximal portion configured to attach to a first bone portion on a first side of a cut in the bone, at least a portion of the proximal portion forming an outer housing,
- a distal portion configured to attach to a second bone portion on a second side of the cut, the first side opposite the second side,
- a motorized drive assembly hermetically sealed within an inner housing arranged within the outer housing, the motorized drive assembly comprising:
  - a memory configured to store prescription information,
  - a power management system comprising at least one charging circuit powered via at least one battery,
  - a wireless receiver configured to receive wireless signals transmitting the prescription information from an external computing device,
  - an electric motor operably coupled to rotate a drive shaft engaged with the distal portion to cause movement of the distal portion away from the proximal portion,
  - an encoder operably coupled to the electric motor, the encoder configured to actuate the electric motor to rotate the drive shaft based on the prescription information.

2. The limb lengthening nail of claim 1, wherein the encoder is configured to semi-continuously actuate the electric motor based on the prescription information.

3. The limb lengthening nail of claim 1, wherein the power management system comprises at least one energy harvesting power source.

4. The limb lengthening nail of claim 3, wherein the at least one energy harvesting power source is configured to harvest energy based on at least one of body heat of the patient or leg movements of the patient.

5. The limb lengthening nail of claim 1, wherein the inner housing comprises a slot and the motor comprises at least one projection configured to engage the slot to prevent rotation of the motor during rotation of the drive shaft.

6. The limb lengthening nail of claim 1, further comprising an optical encoder to monitor engagement between the electric motor and the drive shaft.

7. The limb lengthening nail of claim 6, wherein the optical encoder comprises an infrared optical encoder.

8. The limb lengthening nail of claim 1, wherein an outer diameter of the limb lengthening nail is about 8 to about 10 millimeters.

9. The limb lengthening nail of claim 1, wherein the at least one charging circuit comprises a charge pump circuit having at least one capacitor, the at least one charging circuit to provide power to actuate the motorized drive assembly responsive to a threshold amount of voltage being stored on the at least one capacitor.

10. The limb lengthening nail of claim 1, wherein the prescription information comprises adjustment parameters indicating a length of adjustment over a defined time period.

11. The limb lengthening nail of claim 1, wherein the wireless receiver is configured to transmit wireless signals providing status information to the external computing device.

12. The limb lengthening nail of claim 11, wherein the status information comprises an amount of extension of the limb lengthening nail at a defined time period.

13. The limb lengthening nail of claim 1, wherein the wireless receiver comprises an antenna arranged on an outer surface of the limb lengthening nail.

14. The limb lengthening nail of claim 1, wherein the electric motor is configured to prevent axial rotation of the electric motor.

15. The limb lengthening nail of claim 1, wherein the electric motor is operably coupled to a position sensor to provide continuous or semi-continuous actuation.

* * * * *